United States Patent
Shuman et al.

(10) Patent No.: US 12,171,483 B2
(45) Date of Patent: Dec. 24, 2024

(54) SYSTEM AND METHOD FOR PREDICTABLE DEPLOYMENT OF A MEDICAL DEVICE

(71) Applicant: GYRUS ACMI, INC., Westborough, MA (US)

(72) Inventors: Brandon James Shuman, Westborough, MA (US); Hugo X. Gonzalez, Woodville, WA (US); David H. Dillard, Grapeview, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 17/935,501

(22) Filed: Sep. 26, 2022

(65) Prior Publication Data
US 2023/0055249 A1 Feb. 23, 2023

Related U.S. Application Data

(63) Continuation of application No. 16/865,620, filed on May 4, 2020, now Pat. No. 11,478,296, which is a
(Continued)

(51) Int. Cl.
*A61B 18/14* (2006.01)
*A61B 1/267* (2006.01)
(Continued)

(52) U.S. Cl.
CPC .......... *A61B 18/1477* (2013.01); *A61B 18/14* (2013.01); *A61B 1/2676* (2013.01);
(Continued)

(58) Field of Classification Search
CPC ... A61B 1/2676; A61B 18/14; A61B 18/1477; A61B 18/1492; A61B 2017/00809;
(Continued)

(56) References Cited

U.S. PATENT DOCUMENTS

| | | |
|---|---|---|
| 4,869,259 A | 9/1989 | Elkins |
| 5,427,115 A | 6/1995 | Rowland et al. |

(Continued)

FOREIGN PATENT DOCUMENTS

| | | |
|---|---|---|
| CN | 102225024 A | 10/2011 |
| EP | 2626030 A2 | 8/2013 |

(Continued)

OTHER PUBLICATIONS

"U.S. Appl. No. 14/662,975, Advisory Action mailed Mar. 5, 2019", 3 pgs.

(Continued)

*Primary Examiner* — Tigist S Demie
(74) *Attorney, Agent, or Firm* — Schwegman Lundberg & Woessner, P.A.

(57) ABSTRACT

A medical device system for the delivery of energy to a region of a patient's anatomy is provided. An introducer tube defines a lumen therein and bears a first electrode. A second electrode is movable within the lumen between a retracted position and an extended position. In the retracted position, the second electrode is substantially disposed within the lumen. In the extended position, the second electrode extends at least partially beyond the distal end of the introducer tube. In one form, the introducer tube is configured to substantially hold the second electrode within the lumen in a predetermined orientation in the extended position, and the introducer tube prevents the second electrode from substantially rotating within the lumen of the introducer tube during movement into the extended position. In one form, the introducer tube is more flexible in a first plane than in a second plane.

20 Claims, 11 Drawing Sheets

Related U.S. Application Data continuation of application No. 14/662,975, filed on Mar. 19, 2015, now abandoned.

(60) Provisional application No. 61/972,090, filed on Mar. 28, 2014.

(51) Int. Cl.
 *A61B 17/00* (2006.01)
 *A61B 18/00* (2006.01)

(52) U.S. Cl.
 CPC .............. *A61B 2017/00809* (2013.01); *A61B 2018/00541* (2013.01); *A61B 2018/00577* (2013.01); *A61B 2018/00982* (2013.01); *A61B 2018/1405* (2013.01); *A61B 2018/1435* (2013.01); *A61B 2018/1475* (2013.01); *A61B 18/1492* (2013.01)

(58) Field of Classification Search
 CPC ........... A61B 2018/00541; A61B 2018/00577; A61B 2018/00982; A61B 2018/1405; A61B 2018/1435; A61B 2018/1475
 See application file for complete search history.

(56) References Cited

U.S. PATENT DOCUMENTS

| | | | |
|---|---|---|---|
| 5,507,743 A | 4/1996 | Edwards et al. | |
| 5,672,173 A * | 9/1997 | Gough | A61N 1/06 606/41 |
| 5,855,576 A | 1/1999 | LaVeen et al. | |
| 5,951,547 A | 9/1999 | Gough et al. | |
| 5,980,517 A | 11/1999 | Gough | |
| 6,050,992 A | 4/2000 | Nichols | |
| 6,090,105 A | 7/2000 | Zepeda et al. | |
| 6,379,353 B1 | 4/2002 | Nichols | |
| 6,416,510 B1 | 7/2002 | Altman et al. | |
| 6,551,311 B2 | 4/2003 | Lee et al. | |
| 6,638,277 B2 | 10/2003 | Schaefer et al. | |
| 6,749,604 B1 | 6/2004 | Eggers et al. | |
| 6,929,637 B2 | 8/2005 | Gonzalez et al. | |
| 7,195,629 B2 | 3/2007 | Behl et al. | |
| 7,357,798 B2 | 4/2008 | Sharps et al. | |
| 7,419,488 B2 | 9/2008 | Ciarrocca et al. | |
| 7,434,578 B2 | 10/2008 | Dillard et al. | |
| 7,520,877 B2 | 4/2009 | Lee, Jr. et al. | |
| 7,524,318 B2 | 4/2009 | Young et al. | |
| 7,533,671 B2 | 5/2009 | Gonzalez et al. | |
| 7,691,151 B2 | 4/2010 | Kutsko et al. | |
| 7,842,061 B2 | 11/2010 | Dillard et al. | |
| 7,918,795 B2 | 4/2011 | Grossman | |
| 8,043,286 B2 | 10/2011 | Palanker et al. | |
| 8,073,551 B2 | 12/2011 | Mccann et al. | |
| 8,114,071 B2 | 2/2012 | Woloszko et al. | |
| 8,187,270 B2 | 5/2012 | Auth et al. | |
| 8,361,066 B2 | 1/2013 | Long et al. | |
| 8,656,928 B2 | 2/2014 | Carlson et al. | |
| 11,478,296 B2 | 10/2022 | Shuman et al. | |
| 2002/0042565 A1 | 4/2002 | Cooper et al. | |
| 2003/0028231 A1 | 2/2003 | Partridge et al. | |
| 2003/0199817 A1* | 10/2003 | Thompson | A61M 25/0144 604/95.01 |
| 2003/0233099 A1 | 12/2003 | Danek et al. | |
| 2004/0059328 A1 | 3/2004 | Daniel et al. | |
| 2004/0254572 A1 | 12/2004 | Mcintyre et al. | |
| 2005/0139570 A1 | 6/2005 | Lambert et al. | |
| 2005/0187514 A1 | 8/2005 | Rabiner et al. | |
| 2006/0078501 A1 | 4/2006 | Goertz et al. | |
| 2006/0206111 A1 | 9/2006 | Young | |
| 2007/0043350 A1 | 2/2007 | Soltesz et al. | |
| 2007/0270924 A1 | 11/2007 | Mccann et al. | |
| 2008/0319436 A1* | 12/2008 | Daniel | A61B 18/148 606/41 |
| 2009/0321458 A1 | 12/2009 | Blair et al. | |
| 2010/0004723 A1 | 1/2010 | Foster et al. | |
| 2010/0128608 A1 | 5/2010 | Zou et al. | |
| 2010/0324637 A1 | 12/2010 | Trip et al. | |
| 2011/0238057 A1 | 9/2011 | Moss et al. | |
| 2011/0295262 A1 | 12/2011 | Germain et al. | |
| 2012/0016364 A1 | 1/2012 | Mayse et al. | |
| 2012/0029513 A1 | 2/2012 | Smith et al. | |
| 2012/0052485 A1 | 3/2012 | Shany et al. | |
| 2012/0059247 A1 | 3/2012 | Speeg et al. | |
| 2012/0059308 A1 | 3/2012 | Hsu et al. | |
| 2012/0101380 A1 | 4/2012 | Blum et al. | |
| 2012/0209116 A1 | 8/2012 | Hossack et al. | |
| 2012/0271163 A1 | 10/2012 | Foster et al. | |
| 2012/0316559 A1 | 12/2012 | Mayse et al. | |
| 2013/0085397 A1 | 4/2013 | Ramamurthy et al. | |
| 2013/0190609 A1 | 7/2013 | Fischer, Jr. | |
| 2013/0204068 A1 | 8/2013 | Gnanashanmugam et al. | |
| 2013/0226026 A1 | 8/2013 | Dillard et al. | |
| 2013/0289529 A1 | 10/2013 | Caira et al. | |
| 2013/0310823 A1 | 11/2013 | Gelfand et al. | |
| 2014/0008375 A1 | 1/2014 | Zanus et al. | |
| 2014/0018788 A1 | 1/2014 | Engelman et al. | |
| 2014/0031715 A1 | 1/2014 | Sherar et al. | |
| 2014/0039315 A1 | 2/2014 | Davies et al. | |
| 2014/0066917 A1 | 3/2014 | Cosman, Jr. et al. | |
| 2014/0276764 A1 | 9/2014 | Shuman et al. | |
| 2015/0005769 A1 | 1/2015 | Klink et al. | |
| 2015/0272542 A1 | 10/2015 | Shuman et al. | |
| 2015/0272662 A1 | 10/2015 | Shuman et al. | |
| 2016/0256216 A1 | 9/2016 | Chang et al. | |
| 2020/0261147 A1 | 8/2020 | Shuman et al. | |

FOREIGN PATENT DOCUMENTS

| | | |
|---|---|---|
| EP | 2662116 A1 | 11/2013 |
| EP | 3122233 | 2/2017 |
| JP | 2005523059 | 8/2005 |
| JP | 2005523130 | 8/2005 |
| JP | 2006334242 A | 12/2006 |
| JP | 2007519489 A | 7/2007 |
| JP | 2008526463 | 7/2008 |
| JP | 2011125632 A | 6/2011 |
| JP | 2013502274 A | 1/2013 |
| JP | 2017509395 | 4/2017 |
| JP | 6336611 | 5/2018 |
| JP | 2018140199 | 9/2018 |
| JP | 6632654 | 12/2019 |
| WO | WO-9605123 A1 | 2/1996 |
| WO | WO-9925260 A1 | 5/1999 |
| WO | WO-2011161474 A1 | 12/2011 |
| WO | WO-2012100355 A1 | 8/2012 |
| WO | WO-2013059511 A1 | 4/2013 |
| WO | WO-2013169927 A1 | 11/2013 |
| WO | WO-2013173481 A2 | 11/2013 |
| WO | WO-2015061621 A1 | 4/2015 |
| WO | 2015148265 | 10/2015 |
| WO | WO-2015148077 A1 | 10/2015 |

OTHER PUBLICATIONS

"U.S. Appl. No. 14/662,975, Advisory Action mailed Mar. 6, 2018", 2 pgs.

"U.S. Appl. No. 14/662,975, Advisory Action mailed May 4, 2020", 3 pgs.

"U.S. Appl. No. 14/662,975, Final Office Action mailed Jan. 29, 2020", 11 pgs.

"U.S. Appl. No. 14/662,975, Final Office Action mailed Nov. 28, 2018", 9 pgs.

"U.S. Appl. No. 14/662,975, Final Office Action mailed Dec. 27, 2017", 10 pgs.

"U.S. Appl. No. 14/662,975, Non Final Office Action mailed May 7, 2019", 9 pgs.

"U.S. Appl. No. 14/662,975, Non Final Office Action mailed May 11, 2018", 10 pgs.

"U.S. Appl. No. 14/662,975, Non Final Office Action mailed Jun. 14, 2017", 9 pgs.

(56) References Cited

OTHER PUBLICATIONS

"U.S. Appl. No. 14/662,975, Response filed Feb. 26, 2018 to Final Office Action mailed Dec. 27, 2017", 11 pgs.
"U.S. Appl. No. 14/662,975, Response filed Feb. 27, 2019 to Final Office Action mailed Nov. 28, 2018", 11 pgs.
"U.S. Appl. No. 14/662,975, Response filed Mar. 30, 2020 to Final Office Action mailed Jan. 29, 2020", 9 pgs.
"U.S. Appl. No. 14/662,975, Response filed May 22, 2017 to Restriction Requirement mailed May 4, 2017", 8 pgs.
"U.S. Appl. No. 14/662,975, Response filed Jul. 23, 2018 to Non Final Office Action mailed May 11, 2018", 18 pgs.
"U.S. Appl. No. 14/662,975, Response filed Sep. 12, 2017 to Non Final Office Action mailed Jun. 14, 2017", 8 pgs.
"U.S. Appl. No. 14/662,975, Response filed Sep. 19, 2019 to Non Final Office Action mailed May 7, 2019", 11 pgs.
"U.S. Appl. No. 14/662,975, Restriction Requirement mailed May 4, 2017", 11 pgs.
"U.S. Appl. No. 16/865,620, Non Final Office Action mailed Mar. 16, 2022", 11 pgs.
"U.S. Appl. No. 16/865,620, Notice of Allowance mailed Jun. 23, 2022", 8 pgs.
"U.S. Appl. No. 16/865,620, Response filed Jun. 8, 2022 to Non Final Office Action mailed Mar. 16, 2022", 9 pgs.
"International Application Serial No. PCT/US2014/021473, International Search Report mailed Jul. 2, 2014", 6 pgs.
"International Application Serial No. PCT/US2014/021473, Written Opinion mailed Jul. 2, 2014", 9 pgs.
"International Application Serial No. PCT US2015 021507, International Search Report mailed Nov. 6, 2015", 5 pgs.
"International Application Serial No. PCT US2015 021507, Written Opinion mailed Nov. 6, 2015", 7 pgs.
"International Application Serial No. PCT US2015 021507, International Preliminary Report on Patentability mailed Oct. 13, 2016", 9 pgs.
"European Application Serial No. 15714133.4, Response to Communication pursuant to Rules 161(1) and 162 EPC filed May 18, 2017", 11 pgs.
"European Application Serial No. 15714133.4, Communication Pursuant to Article 94(3) EPC mailed Mar. 13, 2018", 4 pgs.
"European Application Serial No. 15714133.4, Intention to Grant mailed May 7, 2018", 47 pgs.
"Japanese Application Serial No. 2016-554871, Notification of Reasons for Refusal mailed Jul. 28, 2017", w English translation, 12 pgs.
"Japanese Application Serial No. 2016-554871, Response filed Oct. 20, 2017 to Notification of Reasons for Refusal mailed Jul. 28, 2017", w English claims, 11 pgs.
"Japanese Application Serial No. 2016-554871, Notification of Reasons for Refusal mailed Dec. 13, 2017", w English translation, 5 pgs.
"Japanese Application Serial No. 2016-554871, Response filed Mar. 14, 2018 to Notification of Reasons for Refusal mailed Dec. 13, 2017", w English claims, 6 pgs.
"Japanese Application Serial No. 2018-086141, Notification of Reasons for Refusal mailed Apr. 11, 2019", w English translation, 4 pgs.
"Japanese Application Serial No. 2018-086141, Response filed Jun. 20, 2019 to Notification of Reasons for Refusal mailed Apr. 11, 2019", with English claims, 9 pgs.
U.S. Appl. No. 14/662,975, filed Mar. 19, 2015, System and Method for Predictable Deployment of a Medical Device.
U.S. Appl. No. 16/865,620 U.S. Pat. No. 11,478,296, filed May 4, 2020, System and Method for Predictable Deployment of a Medical Device.

* cited by examiner

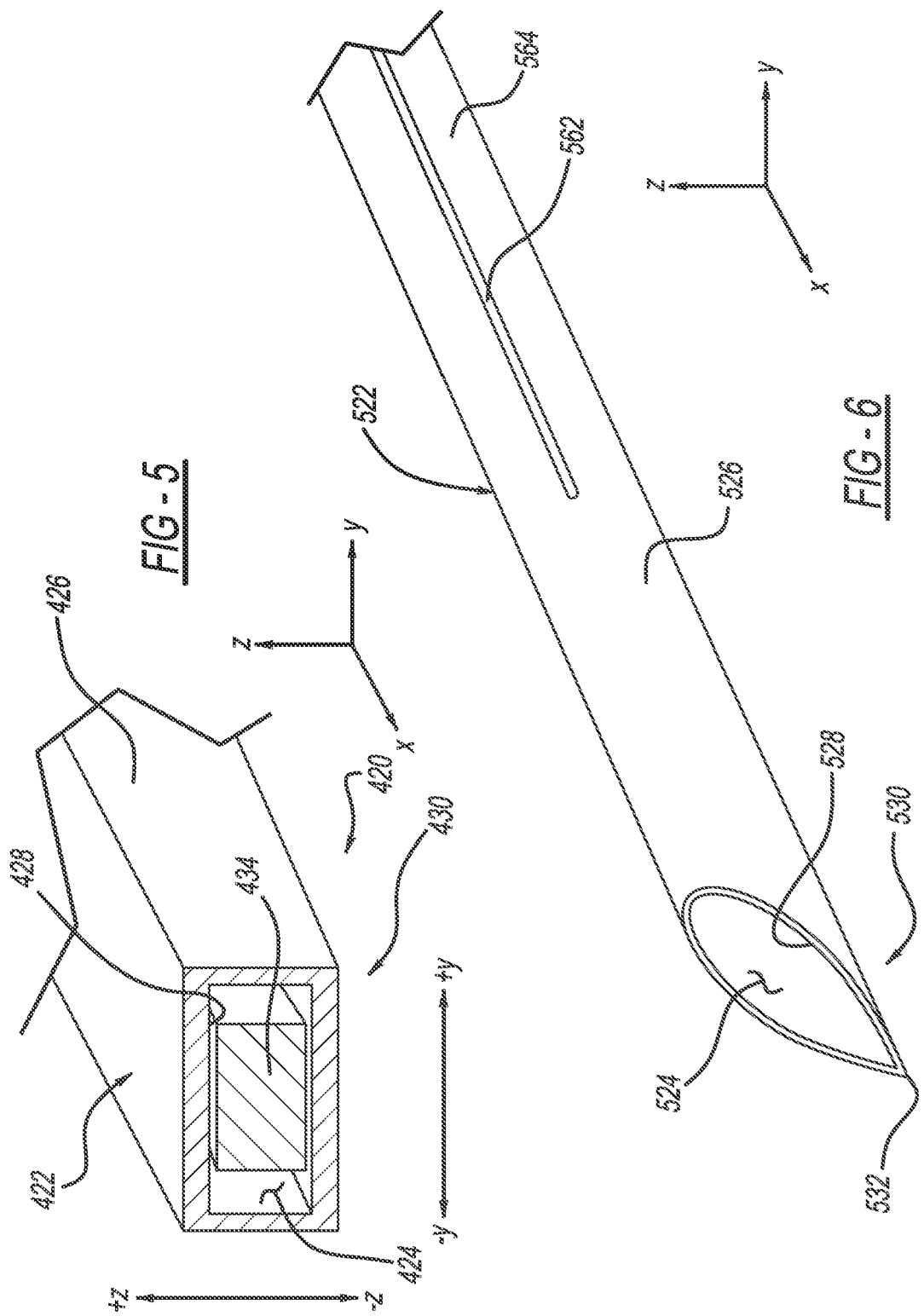

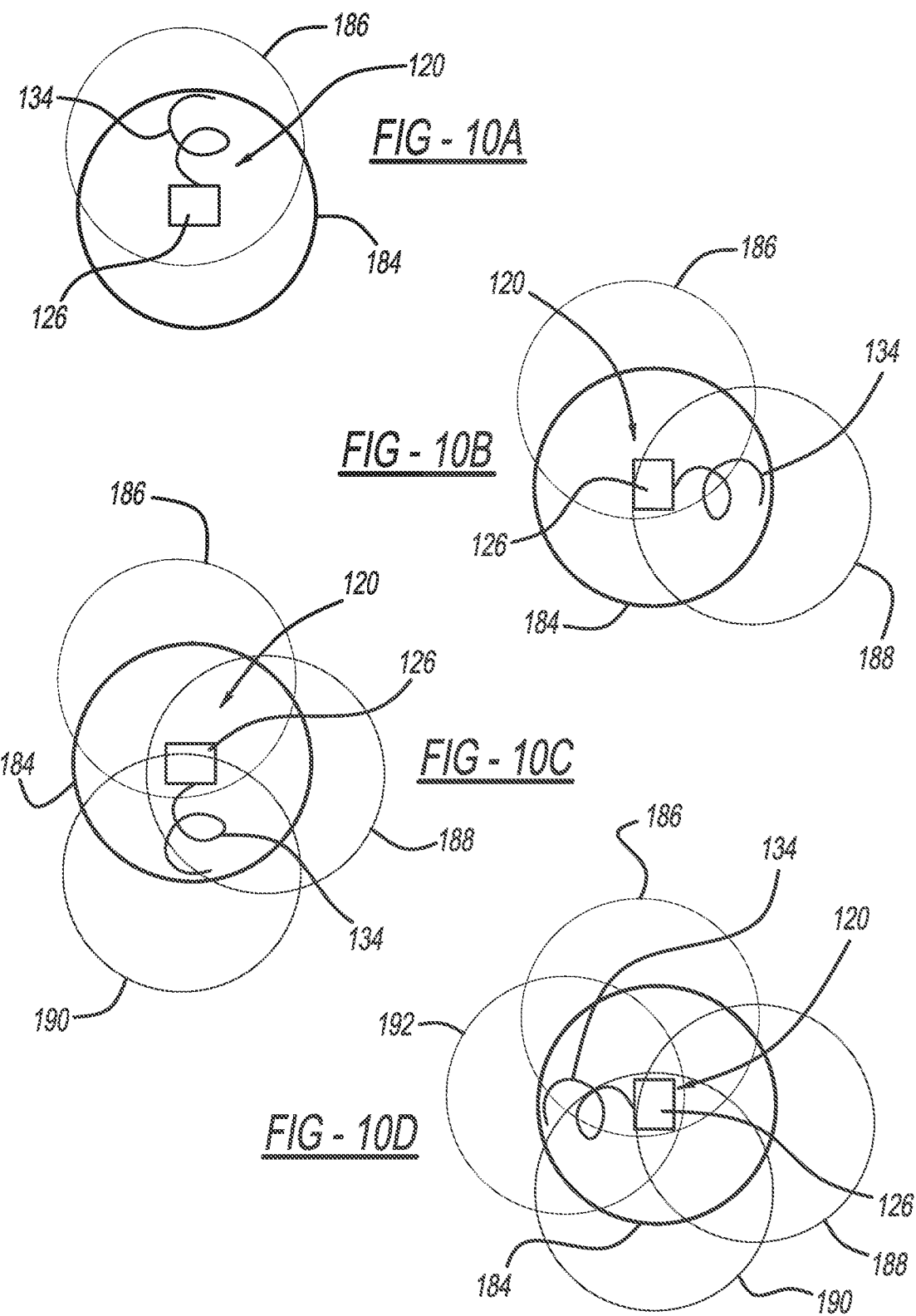

SYSTEM AND METHOD FOR PREDICTABLE DEPLOYMENT OF A MEDICAL DEVICE

RELATED APPLICATIONS

This application is a Continuation of U.S. patent application Ser. No. 16/865,620, filed May 4, 2020, which is a Continuation of U.S. patent application Ser. No. 14/662,975, filed on Mar. 19, 2015, which claims the benefit of U.S. Provisional Patent Application No. 61/972,090, filed on Mar. 28, 2014, the entire contents of which are incorporated herein by reference.

FIELD

The present disclosure relates to medical device systems and methods, and more particularly, to medical device systems, methods, and devices for predictable deployment into a patient's anatomy.

BACKGROUND

The statements in this section merely provide background information related to the present disclosure and may or may not constitute prior art.

Lung nodules, lesions, tumors, and other cancerous or pre-cancerous regions of tissue in the lung may be difficult to treat with invasive surgical techniques, with attendant complications such as excessive bleeding, infection risk, air leaks, pneumothorax, and other such issues. In particular, regions deep in the lung may be difficult to access using conventional methods, further increasing the difficulty of treatment.

Electrical ablation, in particular radiofrequency electrical ablation, has been used in the treatment of tumors and other masses present in solid tissues such as the liver. Use of such techniques, however, entails some attendant complications and difficulties. First, the use of conventional electrical ablation probes in the lungs, requires piercing into the thoracic cavity and into the lung, with a consequent high likelihood of pneumothorax, excessive bleeding and other complications. Moreover, these transthoracic ablation probes are rigid and may not be able to reach certain areas around the pulmonary artery.

While there have been some attempts to pursue radiofrequency electrical ablation via bronchoscopes inserted into airways, these attempts are limited by the confines of the airway passage and the reach of the bronchoscope and accordingly may not be able to position the probes and/or deliver sufficient energy to treat tissue such as lung nodules adequately.

In addition, visualization and localization of the tissue region to be treated may present challenges, especially for tissue regions deep in the lung. Likewise, such visualization within the body may present challenges for procedures in tissue in other areas of the body outside of the lung region. Ultrasound techniques do not always provide for sufficient viewing of the medical devices used. As a result, in ablation procedures, surgeons may be unsure of whether an ablation device has been properly placed and whether adequate ablation has occurred.

SUMMARY

The present disclosure provides systems, methods, and devices for the predictable deployment of medical devices into a patient's anatomy. Predictable deployment may allow for optimal positioning for treatment. The medical device, along with an introducer needle, may have features that cause the medical device to deploy in a predictable direction from the introducer needle. In some versions, the introducer needle may have features that cause the introducer needle to orient in a predictable direction from a surrounding endoscope, such as a bronchoscope.

Accordingly, pursuant to one aspect of the invention, there is contemplated a medical device system for the delivery of energy to a region of a patient's anatomy. The medical device system includes an introducer tube defining a lumen therein. The introducer tube is configured to be inserted into the patient's anatomy. The introducer tube bears a first electrode. A second electrode is movable within the lumen of the introducer tube between a retracted position and an extended position. In the retracted position, the second electrode is substantially disposed within the lumen. In the extended position, the second electrode extends at least partially beyond the distal end of the introducer tube. The first and second electrodes are configured to deliver an energy to a tissue. The introducer tube is configured to substantially hold the second electrode within the lumen in a predetermined orientation in the extended position. The introducer tube prevents the second electrode from substantially rotating within the lumen of the introducer tube during movement into the extended position.

Accordingly, pursuant to another aspect of the invention, there is contemplated a medical device system for the delivery of energy to a region of a patient's anatomy. The medical device system includes an introducer tube defining an introducer tube lumen therein. The introducer tube is configured to be inserted into the patient's anatomy, and the introducer tube bears a first electrode. A second electrode is movable within the introducer tube lumen between a retracted position and an extended position. In the retracted position, the second electrode is substantially disposed within the introducer tube lumen. In the extended position, the second electrode extends at least partially beyond the distal end of the introducer tube. The first and second electrodes are configured to deliver an energy to a tissue. The introducer tube is more flexible in a first plane than in a second plane, wherein the first plane is perpendicular to the second plane.

Accordingly, pursuant to yet another aspect of the invention, there is contemplated a method of delivering energy to a patient's anatomy. The method includes piercing a hollow needle into a tissue in the patient's anatomy, wherein the hollow needle is a first electrode and the hollow needle defines a needle lumen therein having an opening at a distal end. The method also includes extending a second electrode from the distal end of the hollow needle a first time. The method further includes activating the first and second electrodes to deliver a first energy to the tissue through the first electrode and the second electrode. Additionally, the method includes retracting the second electrode into the needle lumen. Further, the method includes rotating the hollow needle by a predetermined number of degrees about a central axis of the distal end of the hollow needle, thus causing the second electrode within the needle lumen to also rotate by substantially the same predetermined number of degrees about the central axis. The method also includes extending the second electrode from the distal end of the hollow needle a second time. In addition, the method includes activating the first and second electrodes to deliver a second energy to the tissue through the first and second electrodes.

The invention may be further characterized by one or any combination of the features described herein, such as: the second electrode being a coil having a collapsed straightened configuration in the retracted position and an expanded helix configuration in the extended position; the coil having a substantially flat cross-sectional shape; the first electrode comprising a piercing tip disposed at the distal end of the first electrode; the piercing tip being configured to pierce through a tissue; the coil being a first coil, the retracted position being a first retracted position, and the extended position being a first extended position, the medical device system further comprising a second coil disposed within the lumen of the introducer tube in a second retracted position; the second coil being movable within the introducer tube between the second retracted position and a second extended position, wherein in the second extended position, the second coil extends at least partially beyond the distal end of the introducer tube; the second coil having a collapsed straightened configuration in the second retracted position and a helix expanded configuration in the second extended position; further comprising a bronchoscope having a curved section disposed at a bronchoscope distal end; the bronchoscope defining a bronchoscope lumen therein; the introducer tube being at least partially disposed in the bronchoscope lumen and axially movable therein; the first electrode being more flexible in a first plane than in a second plane; the second plane being perpendicular to the first plane; wherein a bending orientation of the first electrode aligns with a bend in the curved section of the bronchoscope; the coil having an outer perimeter, a height, and a width in the collapsed straightened configuration; the height and the width being non-equal; the first electrode having a form-fitting inner perimeter defining the lumen; the form-fitting inner perimeter corresponding to the outer perimeter of the coil; the first electrode having a hollow, rectangular cross-section with first, second, third, and fourth sides; the first and third sides being longer than the second and fourth sides; the coil being prevented from substantially rotating within the lumen by at least one of the first, second, third, and fourth sides; the first electrode having a hollow, ovular cross-section; the first electrode having an outer sheath and an inner sheath disposed in the outer sheath; the outer sheath having a round, circular cross-section and the inner sheath defining the lumen; the second electrode being more flexible in the first plane than in the second plane; the first electrode having an outer side having an open channel defined therein; the open channel extending at least partially along a length of the introducer tube; the medical device system further comprising an endoscope having a curved section disposed at an endoscope distal end; the endoscope defining an endoscope lumen therein; the introducer tube being at least partially disposed in the endoscope lumen and axially movable therein; the introducer tube being configured to substantially hold the second electrode within the introducer tube lumen in a predetermined orientation in the extended position, the introducer tube preventing the second electrode from substantially rotating within the introducer tube lumen during movement into the extended position; the method further comprising substantially preventing the second electrode from rotating with respect to the hollow needle when the second electrode is retracted within or extended from the needle lumen; and the method further comprising inserting the hollow needle through an endoscope, the step of rotating the hollow needle by a predetermined number of degrees about a central axis of the distal end of the hollow needle including rotating the endoscope by the predetermined number of degrees about the central axis, thus causing the hollow needle to also rotate by substantially the same predetermined number of degrees about the central axis.

Further aspects, advantages and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 5 is a perspective view of still another medical device system, in accordance with the principles of the present disclosure;

FIG. 6 is a perspective view of yet another introducer tube, in accordance with the principles of the present disclosure;

FIG. 10A is a schematic side view of the medical device system of FIG. 2 performing another variation of the method of FIG. 8 in a first deployment position, in accordance with the principles of the present disclosure;

FIG. 10B is a schematic side view of the medical device system of FIGS. 2 and 10A performing the variation of the method of FIG. 8 started in FIG. 10A in a second deployment position, in accordance with the principles of the present disclosure;

FIG. 10C is a schematic side view of the medical device system of FIGS. 2, 10A, and 10B performing the variation of the method of FIG. 8 started in FIG. 10A in a third deployment position, in accordance with the principles of the present disclosure;

FIG. 10D is a schematic side view of the medical device system of FIGS. 2 and 10A-10C performing the variation of the method of FIG. 8 started in FIG. 10A in a fourth deployment position, in accordance with the principles of the present disclosure;

DETAILED DESCRIPTION

The following description is merely exemplary in nature and is not intended to limit the present disclosure, application, or uses.

The present disclosure provides a system and method for the predictable deployment of a medical device into a patient's anatomy. Predictable deployment may allow for optimal positioning for treatment. The medical device, along with an introducer needle, may have features that cause the medical device to deploy in a predictable direction from the introducer needle. In some versions, the introducer needle may have features that cause the introducer needle to orient in a predictable direction from a surrounding endoscope, such as a bronchoscope.

Figure 1A:
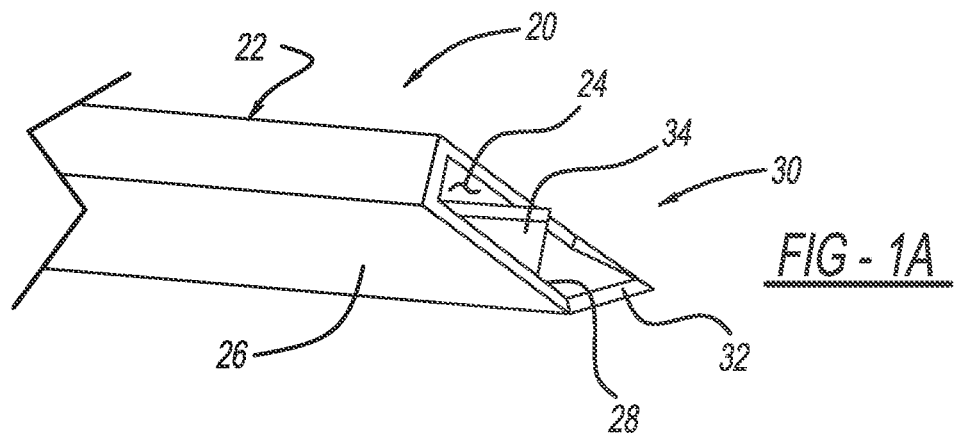
FIG. 1A is a side perspective view of a medical device system including an electrode movably disposed in a retracted position, in accordance with the principles of the present disclosure.
Figure 1B:
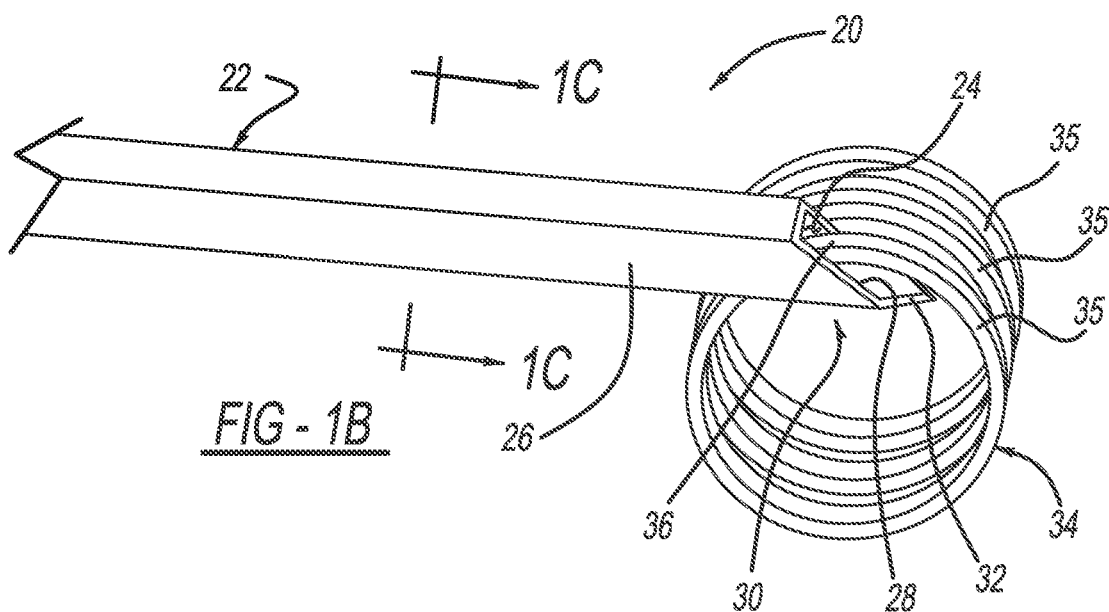
FIG. 1B is a side perspective view of the medical device system of FIG. 1A, the electrode being disposed in an extended position, in accordance with the principles of the present disclosure.
Figure 1C:
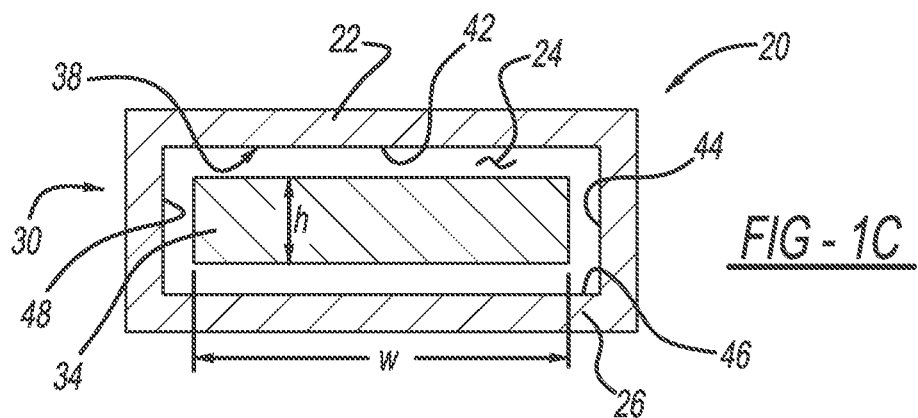
FIG. 1C is a cross-sectional view of the medical device system of FIGS. 1A-1B, taken along the line 1C-1C in FIG. 1B, in accordance with the principles of the present disclosure.

With reference to the figures, wherein like numerals indicate like components, and specifically with reference to FIGS. 1A-1C, an example of a medical device system in accordance with the principles of the present disclosure is illustrated and generally designated at 20. The medical device system 20 is configured to be inserted into a patient's anatomy, for example, for treatment of tissue, such as pulmonary tissue. The medical device system 20 may be configured to be used in bronchoscopic, thoracoscopic, laparoscopic, transcutaneous, and/or percutaneous procedures, by way of example. In some variations, the medical device system 20 may be inserted into a bronchoscope, such as a BF-P180 bronchoscope manufactured by Olympus and/or an EBUS® scope manufactured by Olympus. In some configurations, the medical device system 20 may be inserted into an airway so that the medical device system 20 reaches or is placed proximate a region of tissue to be treated.

The medical device system 20 may include an introducer tube 22, which defines a lumen 24 therein. The introducer tube 22 bears a first electrode 26. As such, the introducer tube 22 may itself be the first electrode 26, as shown in FIGS. 1A-1C, or the first electrode 26 may be attached to the introducer tube 22. The introducer tube 22 defines an opening 28 at a distal end 30 of the introducer tube 22. The introducer tube 22 may be in the form of a hollow needle having a piercing tip 32. The piercing tip 32 may be used to pierce through an airway wall, a tumor, or other tissue, for example, but without limitation. As such, the piercing tip 32 may have a sharp edge or end that may pierce, perforate, or penetrate into or through tissue.

A second electrode 34 is movably disposed in the lumen 24 of the introducer tube 22. FIG. 1A illustrates a retracted position of the second electrode 34. In the retracted position, the second electrode 34 is disposed, or substantially disposed, within the lumen 24 of the introducer tube 22. The second electrode 34 is movable within the introducer tube 22 between the retracted position and an extended position (illustrated in FIG. 1B). When it is desired to extend the second electrode 34 from the introducer tube 22, the second electrode 34 may be pushed or otherwise moved through lumen 24 and out of the opening 28 of the distal end 30 of the introducer tube 22. In the extended position (see FIG. 1B), the second electrode 34 extends at least partially beyond the distal end 30 of the introducer tube 22.

Each of the first and second electrodes 26, 34 has its own electrical lead (not shown) to connect the respective electrode 26, 34 to a power source (not shown). The power source may be connected to the leads via wires and the like. As such, the power source is operable to deliver power to the first electrode 26 and/or the second electrode 34 through the leads (not shown). Thus, the power source may be configured to deliver energy to a region of tissue via the medical device system 20, which includes one or more of the first and second electrodes 26, 34.

In some configurations, the power source (not shown) comprises a source of electric or electromagnetic power. Other sources of energy, alone or in combination, can be used and energy can be delivered to the tissue via the power source (not shown) and/or the medical device system 20. Such power sources can include electric current treatment, cryo treatment (including cryoablation), microwave, laser, and/or photodynamic treatment, by way of example.

In some configurations, the power source may be configured to deliver electric power at varied frequencies. In some configurations, the power source may be configured to deliver radiofrequency (RF) energy in a range of between about 3 KHz and about 300 GHz. In some configurations, the range may be between about 100 KHz and about 500 KHz. In some configurations, the range may be between about 300 KHz and about 400 KHz. In some configurations, the power source may be configured to deliver power in a range of between about 5 watts and about 40 watts, or between about 7 watts and about 25 watts, or between about 8 watts and about 13 watts, by way of example.

In some configurations, the power level may be set by the user or operator, and the resulting voltage and current will vary with that setting. In some configurations, the voltage and current may vary between the ranges of about 20 VAC and about 60 VAC and between about 0.1 ampere and about 1 ampere. In some configurations, the energy delivered to a 1 cm diameter volume treatment site may be between about 8 KJ and about 13 KJ, depending on the type of tissue.

In some configurations, the medical device system 20 may act to heat or ablate tissue via RF energy. Tissues such as tumors (especially lung nodules) or other tissue masses may be treated with energy so as to heat the cells therein to ablate, kill, burn, heat, or denature the cells. The tissue may not necessarily need to be heated so as to kill the component cells, but may be heated enough to modify the cells so as to become non-malignant or otherwise benign. This may also be achieved by cooling, such as by cryoablation.

In some configurations, energy such as RF energy may be delivered by a single electrode, for example, only one of the electrodes 26, 34. In such configurations, the electrical field may emanate away from the electrode as a single point source. A surface pad may serve as a second electrode. In other configurations, energy may be delivered via a bipolar electrode assembly. In such configurations, the electrical field may emanate between two respective poles formed by the first and second electrodes 26, 34. Thus, the first and second electrodes 26, 34 are configured to apply a current, or deliver an energy, to a tissue.

Additional electrodes may be used for multipolar electrode treatment. In the illustrated example, the needle tip serves as the first electrode 26, however, in other configurations, more than two electrodes may be disposed at or near the distal end 30 of the introducer tube 22. In other configurations, multiple medical device systems 20 may be used.

When the second electrode 34 is disposed within the first electrode 26, only the introducer tube 22 may need to be sufficiently strong to pierce through an airway wall (e.g., with the piercing tip 32), rather than needing two separate electrodes possessing sufficient strength or rigidity or being provided with piercing tips arranged to puncture the airway wall. On the other hand, in some configurations, the second electrode 34 may be provided with, or attached to, a piercing end (not shown in FIGS. 1A-1C, see FIG. 2). The piercing end can be used to penetrate into tissue being treated (e.g., a lung nodule). In some configurations, the piercing end may be sheathed by the first electrode 26. In some configurations, the piercing end may be exposed when the second electrode 34 is extended from the first electrode 26.

When the second electrode 34 is extended from the introducer tube 22 and into the extended position, the second electrode 34 may curve or form a spiral, coil, or helix. Such a configuration may be desirable because it may induce an eddy current into the tissue being treated, in addition to the joule heating resulting from a resistance of the tissue being treated. In some configurations, the second electrode 34 is flexible, and adapts a helical, spiral, or coiled configuration once extended away from the distal end 30 of the introducer tube 22. In some configurations, the second electrode 34 may comprise a superelastic material (e.g., Nitinol) and the second electrode 34 can change shapes. Other materials may also be used, including, without limitation, conductive polymers and bundles of multiple wires (such as a cable), which may in some configurations provide for greater elasticity.

As explained above, in some configurations, the second electrode 34 can be manufactured at least in part from a shape-memory material, such as Nitinol. In some such configurations, the second electrode 34 may have an austenite configuration above body temperature that forms a coil or bend. The second electrode 34 may be loaded into the introducer tube 22 in the martensite configuration and in a straighter form, such that heating of the second electrode 34 (e.g., due to electric current passing through the second electrode 34 or by contact of the second electrode 34 with warmer body tissue) causes the second electrode 34 to convert to the austenite configuration and form a bend or coil. In some configurations, the second electrode 34 may be deployed into tissue while still straight, followed by subsequent heating to cause it to change shape. In some configurations, the second electrode 34 may be heated as it is inserted into the tissue (e.g., as it exits the opening 28 of the distal end 30 of the introducer tube 22) so that the second electrode 34 begins to bend or coil as it is deployed. In still other configurations, the second electrode 34 may simply return to a coil shape once deployed by virtue of a spring force in its superelastic material.

It is contemplated that deployment of the second electrode 34 into a bent or coiled configuration may result in the electrode assembly entering a tissue locking position such that a distal end of the second electrode 34 is maintained in position with respect to the treatment area of interest. Such a locking position may be maintained during breathing or heat treatment. It is contemplated that the second electrode 34 may go through multiple deployments from the introducer tube 22 without moving the introducer tube 22, in some variations. The introducer tube 22 may also be formed at least in part of a shape memory material, such as Nitinol, if desired.

Preferably, the second electrode 34 may be shaped as a coil with a pitch in a range of between about 0.1 mm to about 2 mm, and preferably about 1 mm, by way of example. The major diameter of the coil may measure between about 2 mm and about 10 mm, and preferably between about 3 mm and about 4 mm. The coil may also comprise between about 0.5 total helical turns and about 5 total helical turns, and preferably between about 1.5 total helical turns and about 3 total helical turns. The wire diameter that may be used to manufacture the coil may measure between about 0.010 inches and about 0.020 inches, and preferably about 0.015 inches. In the illustrated example, the second electrode 34 forms a coil once deployed within the patient's anatomy. The second electrode 34 has a flat, ribbon shape and defines a plurality of helical turns 35. In this example, three helical turns 35 are illustrated, however, a greater or lower number of helical turns 35 could be used alternatively.

In some configurations, at least one of the first electrode 26 and the second electrode 34 includes an insulating layer (not shown). In some configurations, for example, an insulating layer can be positioned between the first electrode 26 and the second electrode 34, formed on an inner surface of the first electrode 26 and/or on an outer surface of the second electrode 34. Such a placement of the insulating layer(s) can serve to reduce the likelihood of short circuiting between the electrodes 26, 34 while improving the use of bipolar or multipolar ablation configurations.

In some configurations, insulating materials may be lubricious. Lubricious insulating materials can improve the ability of the electrodes 26, 34 to move relative to each other. Any suitable insulating material may be used to overlay at least a portion of the one or more electrodes 26, 34. In some configurations, the insulating material may comprise a polymeric material. For example, PTFE, fluorinated ethylene propylene, high density polyethylene, polyethylene, and/or other suitable insulating materials may be used. In some embodiments, the use of saline (e.g., saline conductive gel) can reduce friction between the electrodes 26, 34. In some embodiments, one or more surfaces of the electrodes 26, 34 can be coated with a ceramic powder.

When using bipolar or multipolar electrical ablation, in particular RF ablation, the first and second electrodes 26, 34 can be used to concentrate the energy being delivered to the surrounding tissue into a zone roughly bounded by these electrodes 26, 34. The degree of extension of the second electrode 34 into the tissue permits the user to modulate the amount and area of energy being directed into the surrounding tissue. In some configurations, the first and second electrodes 26, 34 can be configured to limit the range of relative extension. For example, the range of relative extension between the first and second electrodes 26, 34 can be predetermined based upon the size of the nodule or other area of interest to be treated. In some embodiments, the deployed distance between the first and second electrodes 26, 34 is configured to be approximately equal to the depth of the nodule or other area of interest into which the first and/or second electrodes 26, 34 are deployed. In some configurations, the extent to which the first and second electrodes 26, 34 can move relative to each other in the distal and/or proximal directions is approximately equal to the distance required to move the proximal end of the second electrode 34 from the stored position (retracted position) to the deployed position (extended position). In some embodiments, the extent to which the first and second electrodes 26, 34 can move relative to each other in the distal and/or proximal directions is greater than the deployed distance between the first and second electrodes 26, 34 due, for example, to the second electrode 34 being stored in a relative straight configuration within the lumen 24 of the introducer tube 22 prior to deployment into the extended position.

The introducer tube 22 is configured to substantially hold the second electrode 34 within the lumen 24 in a predetermined orientation in the extended position. A proximal part 36 of the second electrode 34 remains within the lumen 24 in the extended position, and the introducer tube 22 holds the proximal part 36 in a predetermined angular orientation to prevent the second electrode 34 from substantially rotating within the lumen 24 of the introducer tube 22 during movement into the extended position and when the second electrode 34 is in the extended position as shown in FIG. 1B.

For example, referring to FIG. 1C, in the medical device system 20 of FIGS. 1A-1C, the introducer tube 22 has a rectangular hollow cross-section, and the second electrode 34 has a flat, rectangular cross-section. As such, the second electrode 34 is keyed to the introducer tube 22 at least at the distal end 30 of the introducer tube 22. This is because the inner perimeter 38 of the introducer tube 22 corresponds to the outer perimeter 40 of the second electrode 34. Each has a rectangular shape, in this example, and the inner perimeter 38 of the introducer tube 22 is form-fitting, with a sliding fit, over the outer perimeter 40 of the second electrode 34. As such, the portion of the second electrode 34 that is disposed in the lumen 24 is prevented from substantially rotating with respect to the introducer tube 22. In other words, if the second electrode 34 began to rotate within the lumen 24, the second electrode 34 would contact one of the inner sides 42, 44, 46, 48 of the introducer tube 22, which would prevent the second electrode 34 from further rotation.

In the illustrated example, the second electrode 34 cross-section has a height h and a width w, wherein the height h and the width w are non-identical, because the second electrode has an oblong rectangular (non-square rectangular) cross-section. Likewise, the first and third inner sides 42, 46 of the introducer tube 22 are longer than the second and fourth inner sides 44, 48 of the introducer tube 22, creating a hollow rectangular inner cross-section of the introducer tube 22. Thus, the oblong rectangular second electrode 34 fits into the hollow rectangular lumen 24 with a keyed fit that does not substantially rotate. The fit is referred to as a "keyed" fit based on the fact that second electrode 34 has an outer shape that corresponds to, or compliments, the inner perimeter shape of the introducer tube 22, thus preventing substantial rotation therebetween. This causes the second electrode 34 to deploy in a known direction, because it is known how the second electrode 34 is disposed at the distal end 30 of the introducer tube 22. At least the distal end 30 of the introducer tube 22 has the oblong rectangular cross-section, in this example. In some examples, the oblong rectangular cross-section may extend along the length of the introducer tube, while in other examples, the oblong rectangular cross-section may exist only at the distal end 30.

Figure 2:
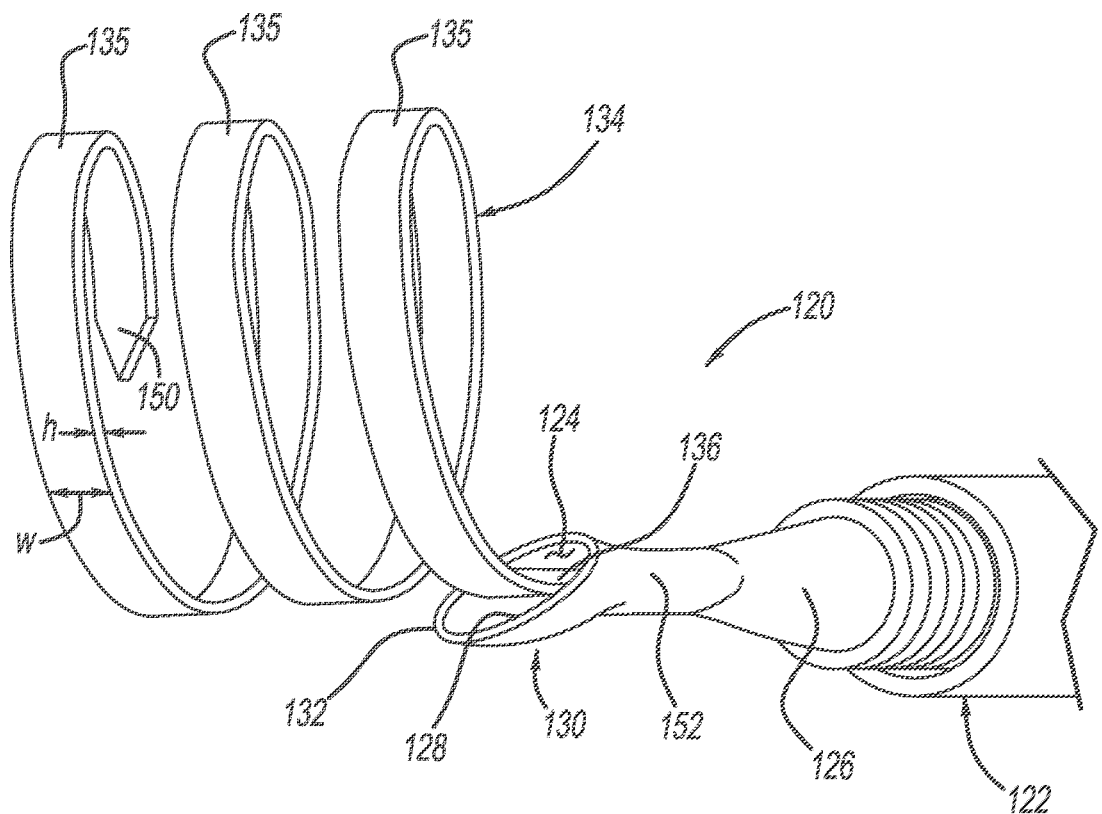
FIG. 2 is a perspective view of another medical device system, in accordance with the principles of the present disclosure.

Referring now to FIG. 2, another example of a medical device system 120 is illustrated. It should be understood that the medical device system 120 may be used similarly to the medical device system 20 described above, if desired. In addition, the medical device system 120 may serve as an electrode assembly, as described above. All other details not described with respect to FIG. 2 may be similar or the same as the features described with respect to the example in FIGS. 1A-1B.

The medical device system 120 has an introducer tube 122, which defines a lumen 124 therein. The introducer tube 122 bears a first electrode 126. As such, the introducer tube 122 may itself be the first electrode 126, as shown in FIGS. 1A-1C, or the first electrode 126 may be attached to the introducer tube 122. The introducer tube 122 defines an opening 128 at a distal end 130 of the introducer tube 122. The introducer tube 122 may be in the form of a hollow needle having a piercing tip 132.

A second electrode 134 is movably disposed in the lumen 124 of the introducer tube 122. FIG. 2 illustrates an extended position of the second electrode 134, though it should be understood that the second electrode 134 may be retracted into a retracted position similar to that shown in FIG. 1A. In the retracted position, the second electrode 134 is disposed, or substantially disposed, within the lumen 124 of the introducer tube 122. The second electrode 134 is movable within the introducer tube 122 between the retracted position (similar to FIG. 1A) and the extended position (illustrated in FIG. 2). When it is desired to extend the second electrode 134 from the introducer tube 122, the second electrode 134 may be pushed or otherwise moved through lumen 124 and out of the opening 128 of the distal end 130 of the introducer tube 122. In the extended position (FIG. 2), the second electrode 134 extends at least partially beyond the distal end 130 of the introducer tube 122.

When the second electrode 134 is disposed within the first electrode 126, only the introducer tube 122 may need to be sufficiently strong to pierce through an airway wall (e.g., with the piercing tip 132), rather than needing two separate electrodes possessing sufficient strength or rigidity or being provided with piercing tips arranged to puncture the airway wall. On the other hand, in some configurations, the second electrode 134 may be provided with, or attached to, a piercing end 150. The piercing end 150 can be used to penetrate into tissue being treated (e.g., a lung nodule). In some configurations, the piercing end 150 may be sheathed by the first electrode 126. In some configurations, the piercing end 150 may be exposed when the second electrode 134 is extended from the first electrode 126.

When the second electrode 134 is extended from the introducer tube 122 and into the extended position, the second electrode 134 may curve or form a spiral, coil, or helix. As described above with respect to FIGS. 1A-1C, the second electrode 134 may comprise a superelastic material (e.g., Nitinol), though other materials may also be used. In the illustrated example, the second electrode 134 forms a coil once deployed within the patient's anatomy. The second electrode 134 may have, for example, a flat, ribbon shape or an ovular shape. The second electrode 134 defines a plurality of helical turns 135. In this example, three helical turns 135 are illustrated, however, a greater or lower number of helical turns 135 could be used alternatively.

The introducer tube 122 is configured to substantially hold the second electrode 134 within the lumen 124 in a predetermined orientation in the extended position. A proximal part 136 of the second electrode 134 remains within the lumen 124 in the extended position, and the introducer tube 122 holds the proximal part 136 in a predetermined angular orientation to prevent the second electrode 134 from substantially rotating within the lumen 124 of the introducer tube 122 during movement into the extended position and when the second electrode 134 is in the extended position as shown in FIG. 2.

For example, in the medical device system 120 of FIG. 2, the introducer tube 122 has a neck portion 152 having an ovular hollow cross-section. The second electrode 134 may have a corresponding ovular cross-section that fits through the neck portion 152, or the second electrode may have a flat, oblong rectangular cross-section that still fits snugly within the neck portion 152. As such, the second electrode 134 is "keyed" to the introducer tube 122 at least at the distal end 130 of the introducer tube 122. This is because the inner perimeter of the neck portion 152 of the introducer tube 122 corresponds to the outer perimeter of the second electrode 134. The inner perimeter of the introducer tube 122 is form-fitting or nearly form-fitting with the outer perimeter of the second electrode 134, whether the second electrode 134 has an oblong rectangular or ovular cross-section. In other words, an ovular cross-section of the second electrode 134 would be more form-fitting than a rectangular cross-section of the second electrode 134 to correspond with the inner perimeter of the neck portion 152. Thus, the portion of the second electrode 134 that is disposed in the lumen 124 is prevented from substantially rotating with respect to the introducer tube 122. In other words, if the second electrode 134 began to rotate within the lumen 124, the second electrode 134 would contact an inner wall in the neck portion 152 of the introducer tube 122, which would prevent the second electrode 134 from further rotation.

In the illustrated example, the second electrode 134 cross-section has a height h and a width w, wherein the height h and the width w are non-identical, because the second electrode 134 has an oblong rectangular or ovular cross-section. Likewise, the inner side of the neck portion 152 of the introducer tube 122 has a longer diameter in one direction than in a perpendicular direction, creating a hollow ovular inner cross-section of the introducer tube 122. Thus, the second electrode 134 fits into the hollow ovular lumen 124 with a keyed fit that does not substantially rotate. This causes the second electrode 134 to deploy in a known direction, because it is known how the second electrode 134 is disposed at the distal end 130 of the introducer tube 122. At least the neck portion 152 of the introducer tube 122 has the ovular cross-section, in this example. In some examples, the ovular cross-section may extend along the length of the introducer tube 122, while in other examples, the ovular cross-section may exist only at the neck portion 152.

Figure 3:
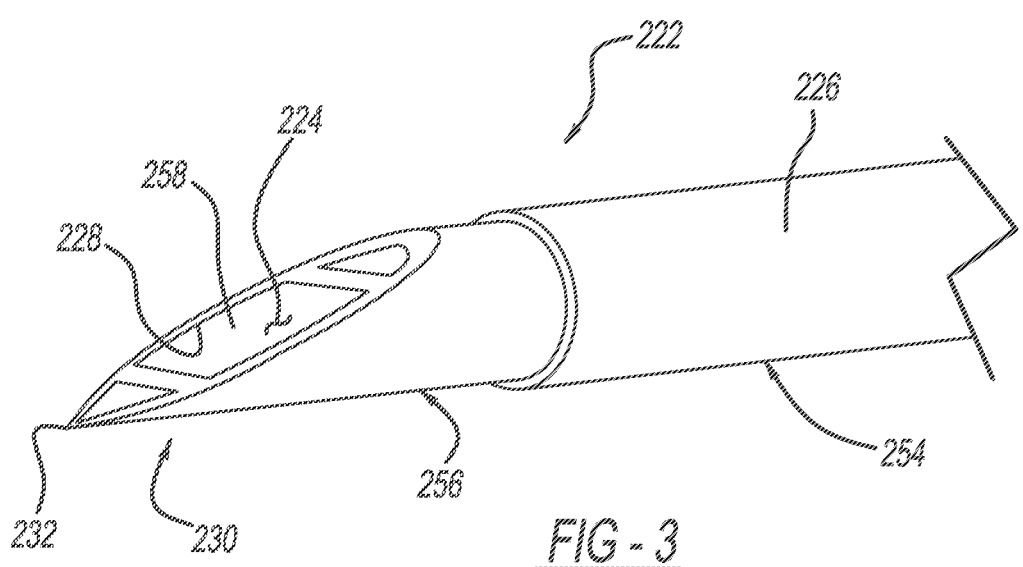
FIG. 3 is a perspective view of an introducer tube, in accordance with the principles of the present disclosure.

Referring now to FIG. 3, another example of an introducer tube 222 for use in a medical device system and with a second electrode is illustrated. It should be understood that the medical device system using the introducer tube 222 may include one of the second electrodes 34, 134 described above, or another suitable second electrode. The introducer tube 222 may be used similarly to those described above, if desired. In addition, the medical device system using the introducer tube 222 may serve as an electrode assembly, as described above. All other details not described with respect to FIG. 3 may be similar or the same as the features described with respect to the example in FIGS. 1A-2.

The introducer tube 222 defines a lumen 224 therein. The introducer tube 222 bears a first electrode 226. In this example, the first electrode 226 is formed from the outer sheath 254. The introducer tube 222 defines an opening 228 at a distal end 230 of the introducer tube 222. The introducer tube 222 may be in the form of a hollow needle having a piercing tip 232.

As described above, a second electrode (not shown) may be movably disposed in the lumen 224 of the introducer tube 222, the second electrode being movable between a retracted position and an extended position.

The introducer tube 222 is configured to substantially hold the second electrode (not shown) within the lumen 224 in a predetermined orientation in the extended position. The introducer tube 222 holds the second electrode in a predetermined angular orientation within the lumen 224 to prevent the second electrode from substantially rotating within the lumen 224 of the introducer tube 222 during movement of the second electrode into the extended position and when the second electrode is in the extended position.

For example, the introducer tube 222 may define the lumen 224 as having an oblong rectangular or ovular cross-section, by way of example. The second electrode may have a corresponding cross-section that fits within the cross-section of the lumen 224 at the distal end 230. As such, the second electrode is "keyed" to the introducer tube 222 at least at the distal end 230 of the introducer tube 222. This is because the inner perimeter of the introducer tube 222 corresponds to the outer perimeter of the second electrode. The inner perimeter of the introducer tube 222 is form-fitting or nearly form-fitting with the outer perimeter of the second electrode, whether the second electrode 134 has an oblong rectangular or ovular cross-section, by way of example. Thus, the portion of the second electrode that is disposed in the lumen 224 is prevented from substantially rotating with respect to the introducer tube 222. In other words, if the second electrode began to rotate within the lumen 224, the second electrode would contact an inner wall of the introducer tube 222, which would prevent the second electrode from further rotation.

In the illustrated example, the introducer tube 222 has an inner sheath 256 surrounded by the outer sheath 254, the inner sheath 256 being disposed in the outer sheath 254. The outer sheath 254 has a round, circular cross-section, in this example, and may be formed of a metal, by way of example. The inner sheath 256 defines the lumen 224, and thus, the inner sheath 256 may have a non-circular inner hollow cross-section defined by an inner wall 258 or walls, in order to key the second electrode within the lumen 224. The inner sheath 256 may be a plastic extrusion, such as from a polyether ether ketone (PEEK) material. The inner sheath 256 may be fixedly attached to the outer sheath 254, for example, by a non-moving form fit.

Figure 4:
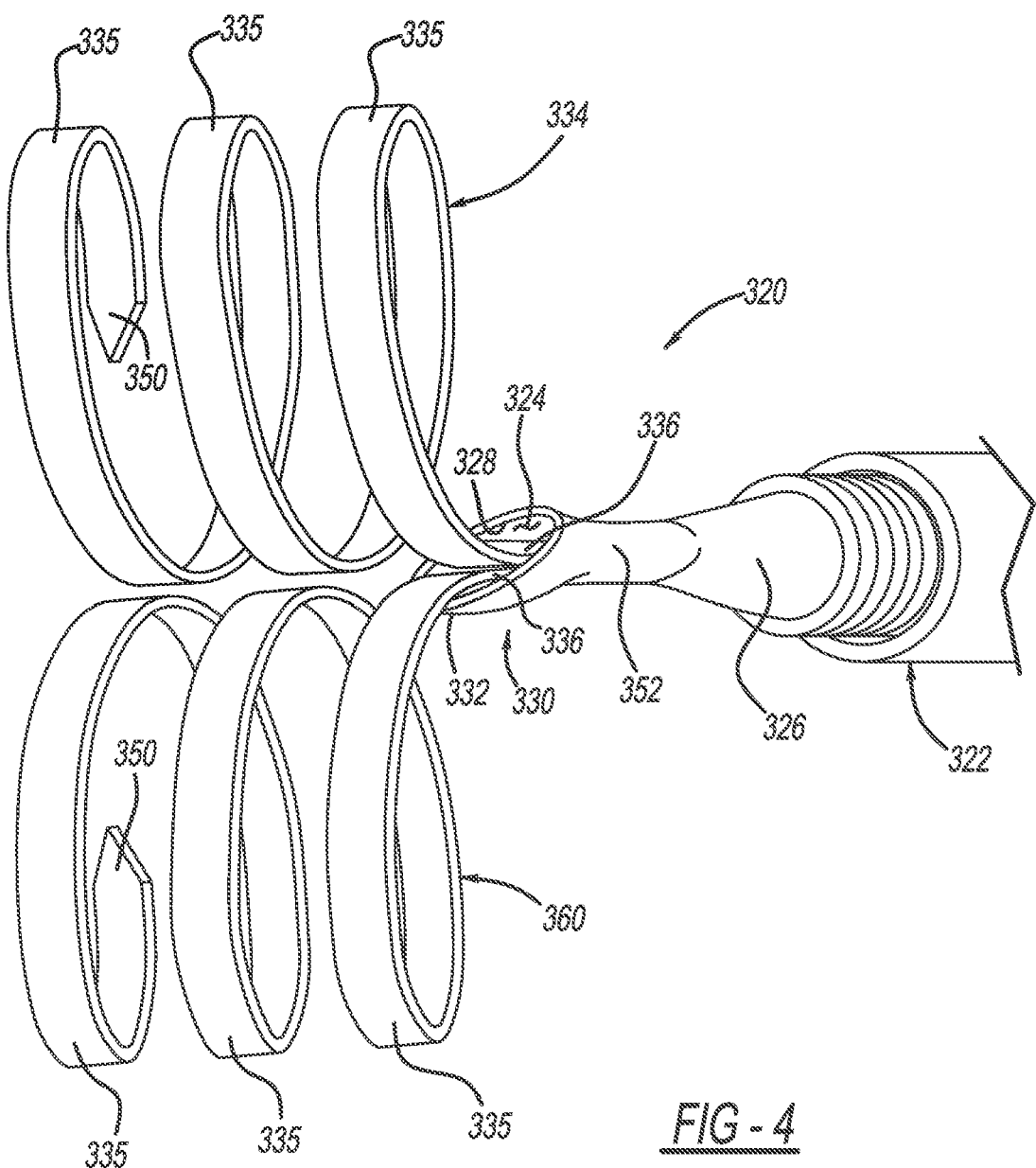
FIG. 4 is a perspective view of yet another medical device system, in accordance with the principles of the present disclosure.

Referring now to FIG. 4, another example of a medical device system 320 is illustrated. It should be understood that the medical device system 320 may be used similarly to the medical device systems 120, 20 described above, if desired. In addition, the medical device system 320 may serve as an electrode assembly, as described above. All other details not described with respect to FIG. 4 may be similar or the same as the features described with respect to the example in FIGS. 1A-3.

The medical device system 320 has an introducer tube 322, which defines a lumen 324 therein. The introducer tube 322 bears a first electrode 326. As such, the introducer tube 322 may itself be the first electrode 326, as shown in FIG. 4, or the first electrode 326 may be attached to the introducer tube 322. The first electrode 326 defines an opening 328 at a distal end 330 of the first electrode 362. The first electrode 326 may be in the form of a hollow needle having a piercing tip 332.

A second electrode 334 is movably disposed in the lumen 324 of the first electrode 326, and a third electrode 360 is movably disposed in the lumen 324 of the introducer tube 322. FIG. 4 illustrates extended positions of the second electrode 334 and the third electrode 360, though it should be understood that the second and third electrodes 334, 360 may be retracted into retracted positions similar to that shown in FIG. 1A. In the retracted positions, the second and third electrodes 334, 360 are disposed, or substantially disposed, within the lumen 324 of the introducer tube 322. The second and third electrodes 334, 360 are movable within the first electrode 326 and the introducer tube 322 between the retracted positions (similar to FIG. 1A) and the extended positions (illustrated in FIG. 4). When it is desired to extend the second and third electrodes 334, 360 from the first electrode 326, the second and third electrodes 334, 360 may be pushed or otherwise moved through lumen 324 and out of the opening 328 of the distal end 330 of the introducer tube 322. In the extended position (FIG. 4), the second and third electrodes 334, 360 extend at least partially beyond the distal end 330 of the first electrode 326. The second and third electrodes 334, 360 may have piercing ends 350.

When the second and third electrodes 334, 360 are extended from the introducer tube 322 and into the extended positions, the second and third electrodes 334, 360 may curve or form a spiral, coil, or helix. As described above with respect to FIGS. 1A-1C, the second and third electrodes 334, 360 may comprise a superelastic material (e.g., Nitinol), though other materials may also be used. In the illustrated example, the second and third electrodes 334, 360 each form a coil once deployed within the patient's anatomy. The second and third electrodes 334, 360 may have, for example, a flat, ribbon shape or an ovular shape. Each of the second and third electrodes 334, 360 define a plurality of helical turns 335. In this example, each electrode 334, 360 has three helical turns 335, however, a greater or lower number of helical turns 335 could be used alternatively.

The introducer tube 322 is configured to substantially hold the second and third electrodes 334 within the lumen 324 in predetermined orientations in the extended positions. In this example, the second electrode 334 extends upwardly from the first electrode 326 in the orientation of FIG. 4, and the third electrode 360 extends downwardly from the first electrode 326 in the orientation of FIG. 4; thus, each electrode 334, 360 reaches a different part of tissue. Proximal parts 336 of the second and third electrode 334, 360 remain within the lumen 324 in the extended positions, and the introducer tube 322 holds the proximal parts 336 in a predetermined angular orientation to prevent the second and third electrodes 334, 360 from substantially rotating within the lumen 324 of the introducer tube 322 during movement into the extended positions and when the second and third electrodes 334, 360 are in the extended positions as shown in FIG. 4.

For example, in the medical device system 320 of FIG. 4, the introducer tube 322 has a neck portion 352 having an ovular hollow cross-section. Each of the second and third electrodes 334, 360 may have corresponding cross-sections that fit together through the neck portion 352, such as ovular or flat cross-sections. As such, the second and third electrodes 334, 360 are keyed to the introducer tube 322 at least at the distal end 330 of the introducer tube 322. This is because the inner perimeter of the neck portion 352 of the introducer tube 322 corresponds to part of the outer perimeters of the second and third electrodes 334, 360. Thus, the portions of the second and third electrodes 334, 360 that are disposed in the lumen 324 are prevented from substantially rotating with respect to the introducer tube 322. In other words, if the second and third electrodes 334, 360 began to rotate within the lumen 324, the second and third electrodes 334, 360 would contact an inner wall in the neck portion 352 of the introducer tube 322, which would prevent the second and third electrodes 334, 360 from further rotation.

The first, second, and third electrodes 326, 334, 360 may be used for multipolar electrode treatment. For example, electricity may pass between the second and third electrodes 334, 360, the second and third electrodes 334, 360 and the first electrode 326, or any combination thereof.

Referring now to FIG. 5, another example of a medical device system 420 is illustrated. It should be understood that the medical device system 420 may be used similarly to the medical device system 20 described above, if desired. In addition, the medical device system 420 may serve as an electrode assembly, as described above. All other details not described with respect to FIG. 5 may be similar or the same as the features described with respect to the examples in FIGS. 1A-4.

The medical device system 420 has an introducer tube 422, which defines a lumen 424 therein. The introducer tube 422 bears a first electrode 426. As such, the introducer tube 422 may itself be the first electrode 426, as shown in FIG. 5, or the first electrode 426 may be attached to the introducer tube 422. The introducer tube 422 defines an opening 428 at a distal end 430 of the introducer tube 422. The introducer tube 422 may be in the form of a hollow needle having a piercing tip (not shown).

A second electrode 434 is movably disposed in the lumen 424 of the introducer tube 422. FIG. 5 illustrates a retracted position of the second electrode 434, though it should be understood that the second electrode 434 may be extended from the first electrode 426 into an extended position similar to that shown in FIG. 1B. In the retracted position, the second electrode 434 is disposed, or substantially disposed, within the lumen 424 of the introducer tube 422. The second electrode 434 is movable within the introducer tube 422 between the retracted position (illustrated in FIG. 5) and the extended position (may be similar to FIG. 1B). When it is desired to extend the second electrode 434 from the introducer tube 422, the second electrode 434 may be pushed or otherwise moved through lumen 424 and out of the opening 428 of the distal end 430 of the introducer tube 422. In the extended position, the second electrode 434 will extend at least partially beyond the distal end 430 of the introducer tube 422.

When the second electrode 434 is extended from the introducer tube 422 and into the extended position, the second electrode 434 may curve or form a spiral, coil, or helix, as shown above in FIGS. 1B, 2, and 4. As described above with respect to FIGS. 1A-1C, the second electrode 434 may comprise a superelastic material (e.g., Nitinol), though other materials may also be used. In the illustrated example, the second electrode 434 forms a coil once deployed within the patient's anatomy. The second electrode 434 may have, for example, a flat, ribbon shape as shown, or another suitable shape. Once deployed, the second electrode 434 defines a plurality of helical turns (not shown).

The introducer tube 422 is configured to substantially hold the second electrode 434 within the lumen 424 in a predetermined orientation in the extended and the retract positions, in this variation. The introducer tube 422 holds the second electrode 434 in a predetermined angular orientation to prevent the second electrode 434 from substantially rotating within the lumen 424 of the introducer tube 422 during movement into the extended position and when the second electrode 434 is in the retracted position (as shown in FIG. 5) and the extended position (not shown).

For example, in the medical device system 420 of FIG. 5, the introducer tube 422 has a rectangular hollow cross-section, and the second electrode 434 has a flat, rectangular cross-section, similar to the cross-sections described in FIG. 1C, and discussion with respect to FIG. 1C is herein incorporated by reference into this section. As such, the second electrode 434 is keyed to the introducer tube 422 at least at the distal end 430 of the introducer tube 422.

In the illustrated example, the introducer tube 422 is more flexible in a first plane than in a second plane, wherein the first plane is perpendicular to the second plane. More specifically, per convention, X-Y-Z coordinates are illustrated with the Y-direction extending to the left and right in the orientation of FIG. 5, the Z-direction extending up and down in the orientation of FIG. 5, and the X-direction extending out of and into the page in the orientation of FIG. 5. The first electrode 426 is more flexible in the X-Z plane, or in the positive and negative Z-directions, than in the Y-Z plane or in the positive and negative Y-directions.

Likewise, the second electrode 434 may be more flexible in the first plane than in the second plane. Thus, in this example, the second electrode 434 is more flexible in the X-Z plane, or in the positive and negative Z-directions, than in the Y-Z plane or in the positive and negative Y-directions. Accordingly, the second electrode 434 is keyed to the first electrode 426 by virtue of the second electrode 434 being bendable in one plane (the X-Z plane here), while being substantially unbendable in other planes. Thus, the second electrode 434 will tend to only bend in the plane in which it is bendable. If the first electrode 426 is bent around a curve, which will be described in further detail below, the second electrode 434 will only bend along its bendable plane around the curve, and thus, an operator will know which direction the second electrode 434 is deployed.

Referring now to FIG. 6, another example of an introducer tube 522 for use in a medical device system and with a second electrode is illustrated. It should be understood that the medical device system using the introducer tube 522 may include one of the second electrodes 34, 134, 434 described above, or another suitable second electrode. The introducer tube 522 may be used similarly to those described above, if desired. In addition, the medical device system using the introducer tube 522 may serve as an electrode assembly, as described above. All other details not described with respect to FIG. 6 may be similar or the same as the features described with respect to the examples in FIGS. 1A-5.

The introducer tube 522 defines a lumen 524 therein. The introducer tube 522 bears a first electrode 526. In this example, the first electrode 526 is the introducer tube 522 itself. The introducer tube 522 defines an opening 528 at a distal end 530 of the introducer tube 522. The introducer tube 522 may be in the form of a hollow needle having a piercing tip 532.

As described above, a second electrode (not shown) may be movably disposed in the lumen 524 of the introducer tube 522 between a retracted position and an extended position.

The introducer tube 522 is configured to substantially hold the second electrode (not shown) within the lumen 524 in a predetermined orientation in the extended position. The introducer tube 522 holds the second electrode in a predetermined angular orientation within the lumen 524 to prevent the second electrode from substantially rotating within the lumen 524 of the introducer tube 522 during movement of the second electrode into the extended position and when the second electrode is in the extended position.

The introducer tube 522 has an open channel 562 defined in outer side 564 of the introducer tube 522. The open channel 562 may extend entirely through the outer side 564 of the introducer tube 522, or the open channel 562 may be a groove, cavity, or score mark in the outer side 564 without extending completely through the outer side 564 and into the lumen 524. The open channel 562 renders the introducer tube 522 more bendable along a first plane than along a second plane that is perpendicular to the first plane. More specifically, per convention, X-Y-Z coordinates are illustrated with the Y-direction extending to the left and right in the orientation of FIG. 6, the Z-direction extending up and down in the orientation of FIG. 6, and the X-direction extending out of and into the page in the orientation of FIG. 6. The first electrode 526 is more flexible in the X-Z plane, or in the positive and negative Z-directions, than in the Y-Z plane, or in the positive and negative Y-directions.

Likewise, the second electrode (not shown) may be more flexible in the first plane than in the second plane. The second electrode (not shown) could also have an open channel, groove, cavity, or score formed therein. Accordingly, the second electrode could be keyed to the first electrode 526 by virtue of the second electrode being bendable in one plane (the X-Z plane here), while being substantially unbendable in other planes. Thus, the second electrode will tend to only bend in the plane in which it is bendable.

The open channel 562 may also serve as a keyway to orient the second electrode (not shown) within the first electrode 526, in some variations.

Figure 7:
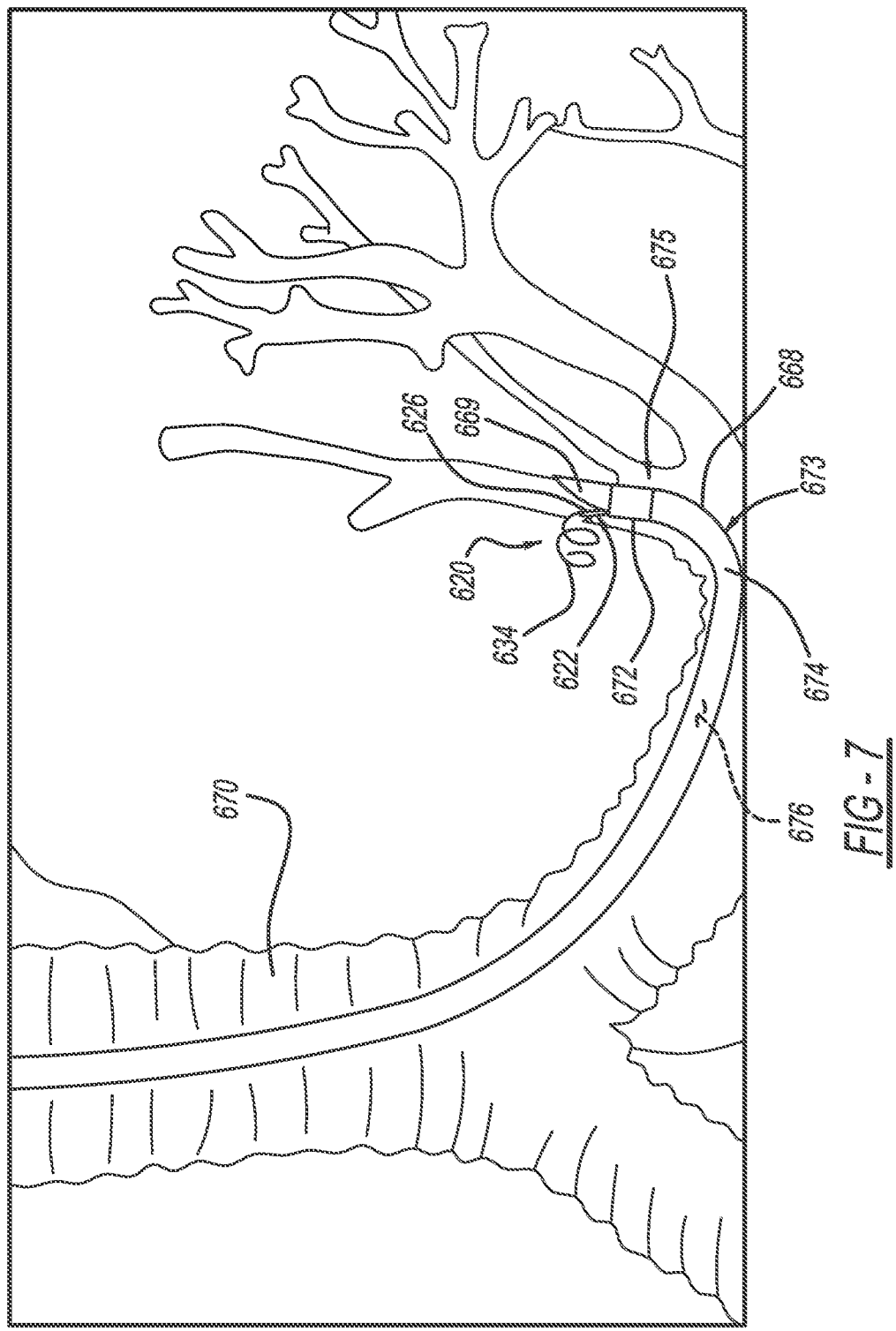
FIG. 7 is a side view of still another medical device system, the medical device system being deployed in an airway through a bronchoscope, in accordance with the principles of the present disclosure.

FIG. 7 illustrates an embodiment of a medical device system 620 disposed within a bronchoscope 668 provided with a side-facing ultrasound probe 669 placed within an airway 670. An example of such a bronchoscope 668 is the EBUS® scope manufactured by Olympus. Preferably, the bronchoscope 668 is provided with at least one lateral port 672 extending from the bronchoscope working channel or lumen 676; this permits the introducer tube 622 (bearing the first electrode 626) to extend through the port 672. The bronchoscope 668 has a curved section 673 defining a bend 674 therein. The curved section 673 is disposed at or near a distal end 675 of the bronchoscope, which terminates in the port 672. The introducer tube 622 is at least partially disposed in the bronchoscope lumen 676 and axially movable therein.

In some configurations, the first electrode 626 is bendable and flexible. In some configurations, the first electrode 626 may be bendable at an angle of at least 10°, preferably about 20°, about 30°, about 45°, about 55°, about 65°, about 75°, and even more preferably at least about 90°, relative to the longitudinal axis of the axial length of the airway. As such, when a region of lung tissue to be treated is located, the first electrode 626 can be extended at least partially into that region of lung tissue by piercing through the airway 670. As described above in reference to previous embodiments, a second electrode 634 in the form of a coil is movable from a retracted position into an extended position as shown.

Like the examples in FIGS. 5-6 (which may be used in FIG. 7), the introducer tube 622 is more flexible in a first plane than in a second plane, wherein the first plane is perpendicular to the second plane. Accordingly, as the medical device system 620 is moved around the bend 674 in the bronchoscope 668 (or other endoscope for other applications), the introducer tube 622 automatically orients itself in the direction in which the introducer tube 622 is most flexible to go around the bend 674. In some variations, a bend may be located in the port 672. Thus, a bending orientation of the first electrode 626 aligns with the bend 674 in the curved section 673 of the bronchoscope 668, or with a bend located in the port 672 in other embodiments. Accordingly, an operator can then know the orientation in which the medical device system 620 is extending from the port 672 of the bronchoscope 668. If the second electrode 634 is keyed within the first electrode 626 (in any of the manners described above, for example), then the operator will also know the orientation in which the second electrode 634 will deploy from the first electrode 626.

Figure 8:
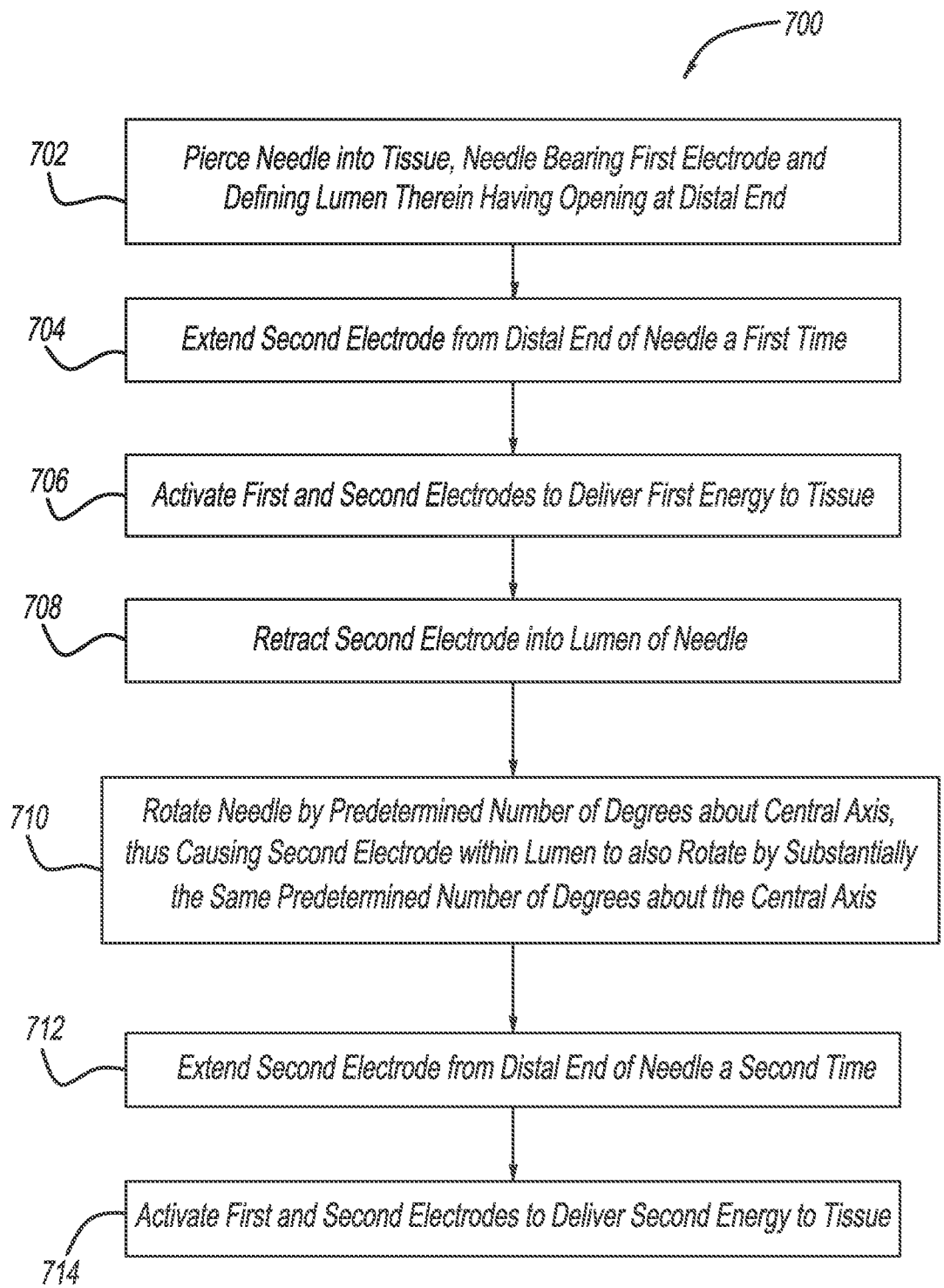
FIG. 8 is a block diagram illustrating a method of delivering energy to a patient's anatomy, in accordance with the principles of the present disclosure.
Figure 9A:
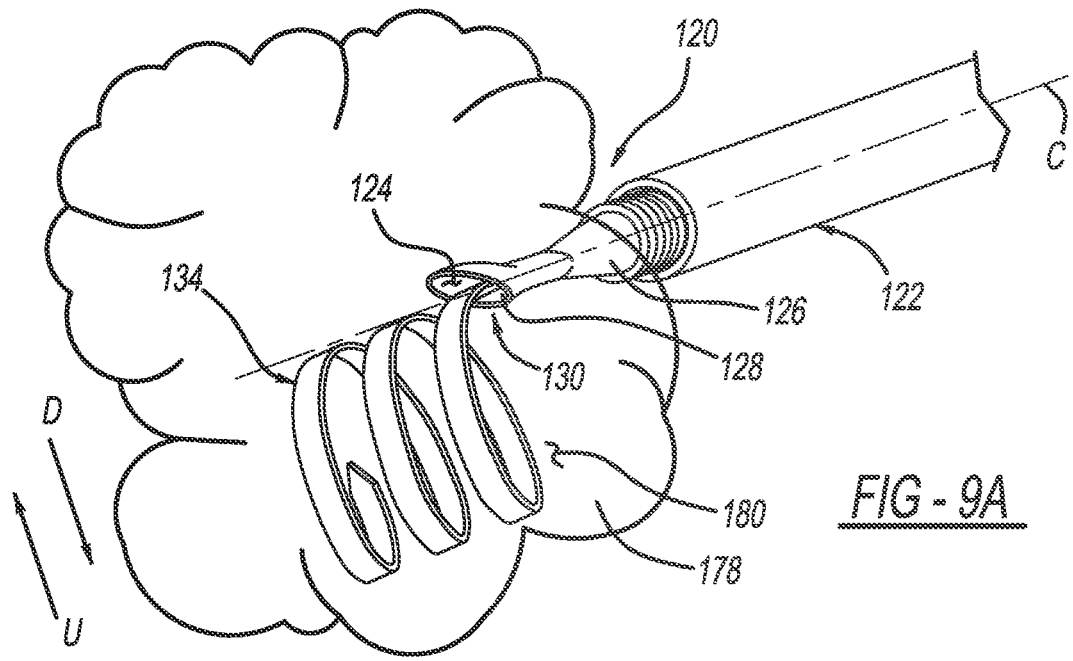
FIG. 9A is a perspective view of the medical device system of FIG. 2 performing a variation of the method of FIG. 8 in a first deployment position, in accordance with the principles of the present disclosure.
Figure 9B:
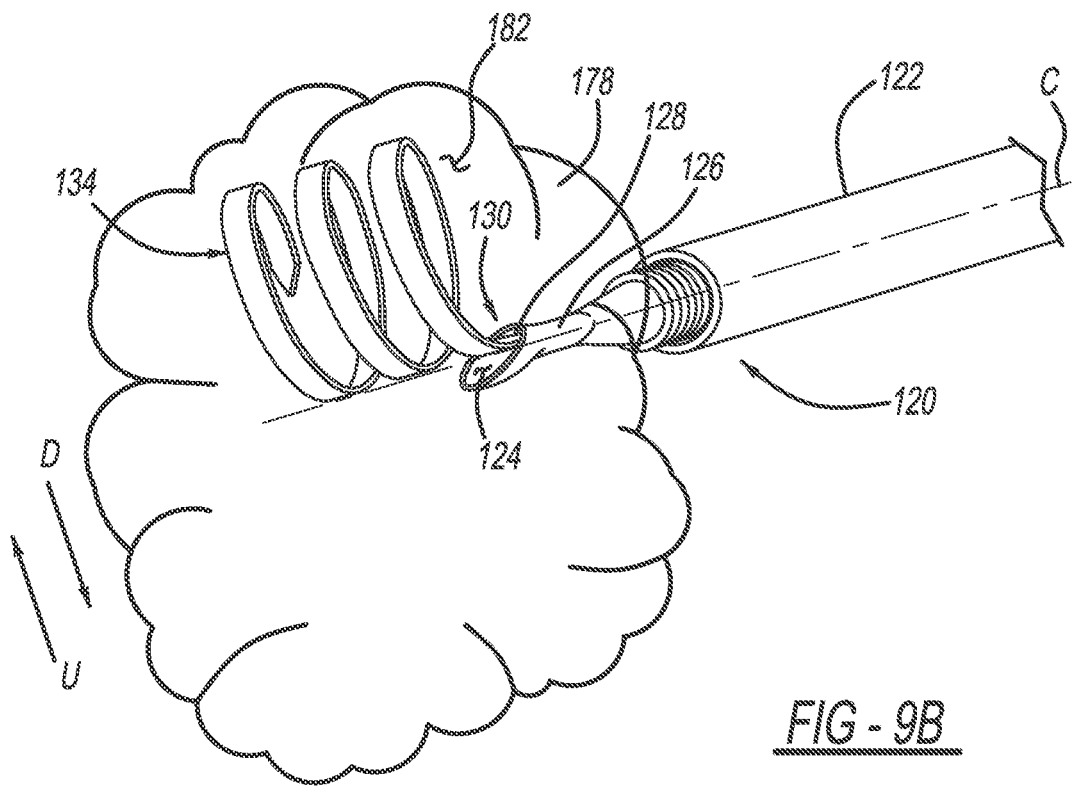
FIG. 9B is a perspective view of the medical device system of FIGS. 2 and 9A performing the variation of the method of FIG. 8 started in FIG. 9A in a second deployment position, in accordance with the principles of the present disclosure.

Referring now to FIG. 8 and FIGS. 9A-9B, a method of delivering energy to a patient's anatomy is illustrated and generally designated at 700. The method 700 includes a first step 702 of piercing a hollow needle into a tissue in the patient's anatomy, wherein the hollow needle is a first electrode and the hollow needle defines a needle lumen therein having an opening at a distal end. Any of the medical device systems 20, 120, 320, 420, 620 and/or introducer tubes 22, 122, 222, 322, 422, 522, 622 hereinbefore shown and described, or another suitable medical device system, may be used in the method 700. For illustration purposes, however, FIGS. 9A and 9B show the medical device assembly 120 hereinbefore described with respect to FIG. 2 being used to perform the method 700. Thus, referring to FIG. 9A, the hollow needle, or introducer tube 122, is pierced into a tissue 178. The introducer tube 122 bears the first electrode 126 at a distal end 130, and the introducer tube 122 defines a lumen 124 therein having an opening 128 at the distal end 130.

The method 700 also includes a step 704 of extending a second electrode from the distal end of the hollow needle a first time. Thus, as shown in FIG. 9A, the second electrode 134 is pushed out of the opening 128 to extend from the distal end 130 of the hollow needle, or electrode 126 and introducer tube 122, a first time. Note that the second electrode 134 extends in a downward direction D from a central axis C in the orientation of FIG. 9A upon being deployed from the first electrode 126 the first time. Such orientation is predictable, based on the second electrode 134 being keyed to the first electrode 126, as described above.

The method 700 further includes a step 706 of activating the first electrode 126 and the second electrode 134 to deliver a first energy to the tissue 178 through the first electrode 126 and the second electrode 134. Accordingly, the electrodes 126, 134 will ablate the tissue 178 in an area near the first and second electrodes 126, 134, which is shown in a first region 180 of the tissue 178 in FIG. 9A. The method 700 then includes a step 708 of retracting the second electrode 134 into the needle lumen 124, which may be into a retracted position similar to that illustrated in FIG. 1A.

The method 700 includes a step 710 of rotating the hollow needle 122 by a predetermined number of degrees about the central axis C of the distal end 130 of the hollow needle 122. Such rotation of the hollow needle, or introducer tube 122, causes the second electrode 134 within the needle lumen 124 to also rotate by substantially the same predetermined number of degrees about the central axis C by virtue of the fact that the second electrode 134 is keyed in the lumen 124, for example, in one or more of the ways described above. In this case, the rotation occurs from the orientation of FIG. 9A to the orientation of FIG. 9B. As can be seen, the introducer tube 122 and first electrode 126 have been rotated about 180° about the central axis C. Thus, the method 700 may include substantially preventing the second electrode 134 from rotating with respect to the hollow needle 122 when the second electrode 134 is retracted within or extended from the needle lumen 124.

Referring to FIGS. 8 and 9B, the method 700 further includes a step 712 of extending the second electrode 134 from the distal end 130 of the hollow needle 122 a second time. Since the second electrode 134 was held to the orientation of the first electrode 126, when the first electrode 126 was rotated about 180°, the second electrode 134 was also rotated about 180° with the first electrode 126. Thus, when the second electrode 134 is extended from the distal end 130 a second time, the second electrode 134 then extends in an upward direction U from the central axis C, in the orientation of FIG. 9B.

The method 700 includes a step 714 of activating the first and second electrodes 126, 134 to deliver a second energy to the tissue 178 through the first and second electrodes 126, 134. Accordingly, the electrodes 126, 134 will ablate the tissue 178 in an area near the first and second electrodes 126, 134, which is shown in a second region 182 of the tissue 178 in FIG. 9B.

The method 700 could also include inserting the hollow needle through an endoscope, such as the bronchoscope 668 of FIG. 7. In such a variation, the step 710 of rotating the hollow needle 122 by a predetermined number of degrees about the central axis C of the distal end 130 of the hollow needle 122 may include rotating the endoscope (in this example, bronchoscope 668) by the predetermined number of degrees about the central axis C, thus causing the hollow needle 122 to also rotate by substantially the same predetermined number of degrees about the central axis C. In other words, in this variation, bronchoscope 668 or other endoscope is rotated by the physician, while both the introducer tube 122 and the second electrode 134 merely rotate by virtue of the fact that they are ultimately keyed to the bronchoscope 668.

Referring now to FIGS. 10A-10D, the method 700 is shown implemented with additional steps and with the second electrode 134 deployed in additional orientations. In FIG. 10A, the medical device system 120 is inserted into a tissue 184, and the second electrode 134 is extended from the first electrode 126. A first ablation is performed, including activating the first and second electrodes 126, 134, and as such, the medical device system 120 ablates an area denoted by the first lighter circle 186.

After the first ablation, the second electrode 134 may be retracted into the first electrode 126, for example, as in FIG. 1A. The first electrode 126 is then rotated about 90° to the orientation shown in FIG. 10B. The second electrode 134 automatically rotates with the first electrode 126, being keyed together, for example, in one of the ways described above. The second electrode 134 is then extended from the first electrode 126 a second time in a second direction. A second ablation is performed, including activating the first and second electrodes 126, 134, and as such, the medical device system 120 ablates an area denoted by the second lighter circle 188. FIG. 10B illustrates that areas 186 and 188 have thus far been ablated.

After the second ablation, the second electrode 134 may be retracted into the first electrode 126, for example, as in FIG. 1A. The first electrode 126 is then rotated about 90° to the orientation shown in FIG. 10C. The second electrode 134 automatically rotates with the first electrode 126, being keyed together, for example, in one of the ways described above. The second electrode 134 is then extended from the first electrode 126 a third time in a third direction. A third ablation is performed, including activating the first and second electrodes 126, 134, and as such, the medical device system 120 ablates an area denoted by the third lighter circle 190. FIG. 10C illustrates that areas 186, 188, and 190 have thus far been ablated.

After the third ablation, the second electrode 134 may be retracted into the first electrode 126, for example, as in FIG. 1A. The first electrode 126 is then rotated about 90° to the orientation shown in FIG. 10D. The second electrode 134 automatically rotates with the first electrode 126, being keyed together, for example, in one of the ways described above. The second electrode 134 is then extended from the first electrode 126 a fourth time in a fourth direction. A fourth ablation is performed, including activating the first and second electrodes 126, 134, and as such, the medical device system 120 ablates an area denoted by the fourth lighter circle 192. FIG. 10D illustrates that areas 186, 188, 190, and 192 have now been ablated. Areas 186, 188, 190, 192 cover the entire area of the target tissue 184, and therefore, the method resulted in the full ablation of the target tissue 184.

Figure 11A:
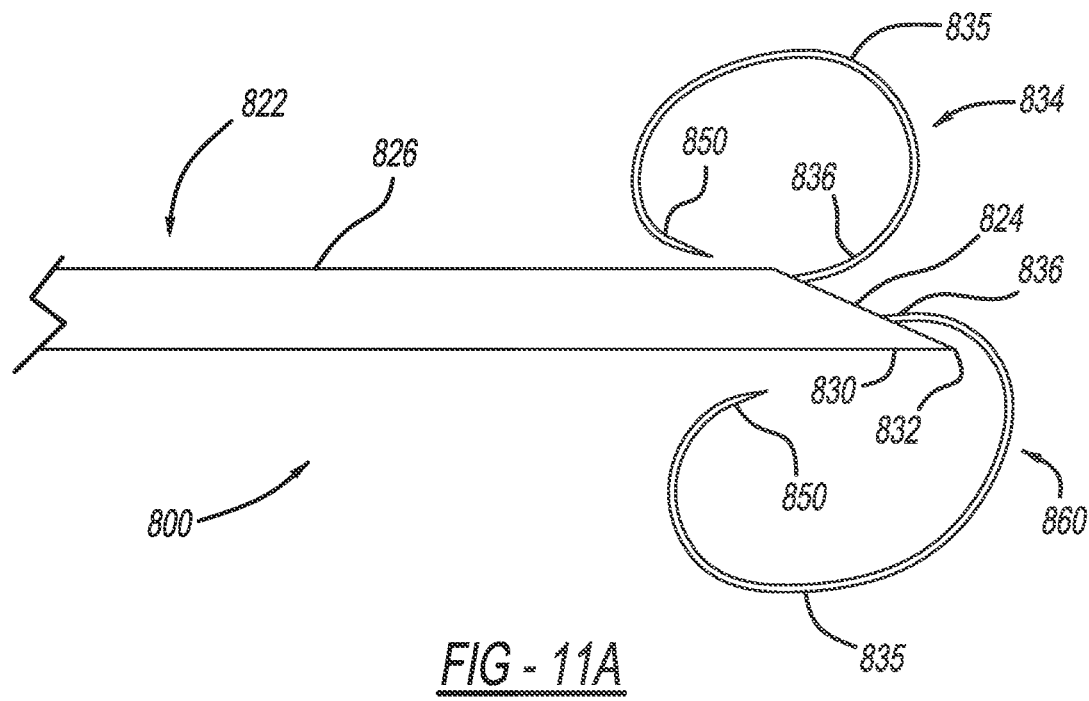
FIG. 11A is a schematic side view of a yet another medical device system, in accordance with the principles of the present disclosure.
Figure 11B:
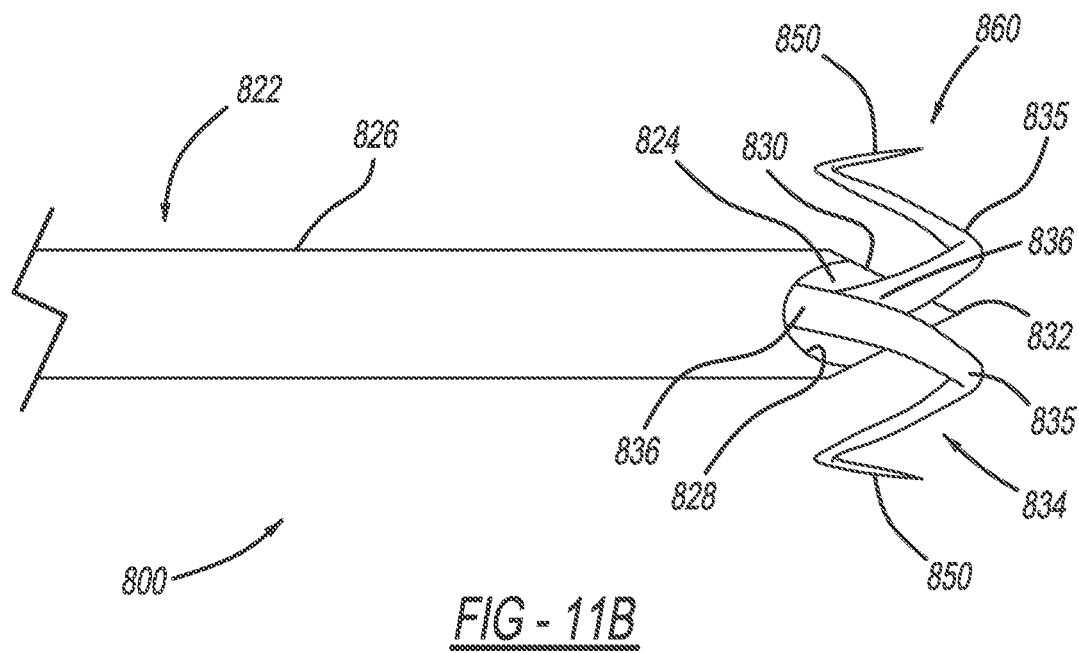
FIG. 11B is a schematic top view of the medical device system of FIG. 11A, in accordance with the principles of the present disclosure.
Figure 12:
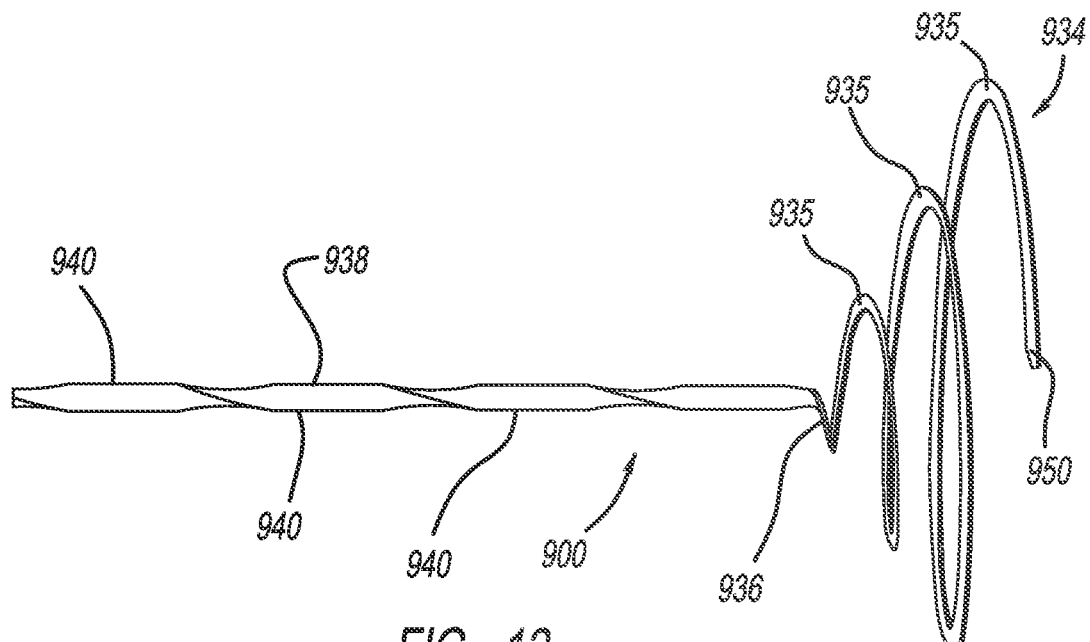
FIG. 12 is a schematic side view of an electrode, in accordance with the principles of the present disclosure.

Turning now to FIGS. 11A and 11B, another example of a medical device system 800 is illustrated. It should be understood that the medical device system 800 may be used similarly to the medical device systems 120, 20, 320 and 420, as well as the introducer tubes 222 and 522, described above, if desired. In addition, the medical device system 800 may serve as an electrode assembly, as described above. All other details not described with respect to FIGS. 11A and 11B may be similar or the same as the features described with respect to the example in FIGS. 1A-6.

The medical device system 800 has an introducer tube 822, which defines a lumen 824 therein. The introducer tube 822 bears a first electrode 826. As such, the introducer tube 822 may itself be the first electrode 826, as shown in FIGS. 11A and 11B, or the first electrode 826 may be attached to the introducer tube 822. The first electrode 826 defines an opening 828 at a distal end 830 of the first electrode 826. The first electrode 826 may be in the form of a hollow needle having a piercing tip 832.

A second electrode 834 is movably disposed in the lumen 824 of the introducer tube 822, and a third electrode 860 is movably disposed in the lumen 824 of the introducer tube 822. FIGS. 11A and 11B illustrate extended positions of the second electrode 834 and the third electrode 860, though it should be understood that the second and third electrodes 834, 860 may be retracted into retracted positions similar to that shown in FIG. 1A. In the retracted positions, the second and third electrodes 834, 860 are disposed, or substantially disposed, within the lumen 824 of the introducer tube 822. The second and third electrodes 834, 860 are movable within the first electrode 826 and the introducer tube 822 between the retracted positions (similar to FIG. 1A) and the extended positions (illustrated in FIGS. 11A and 11B). When it is desired to extend the second and third electrodes 834, 860 from the first electrode 826, the second and third electrodes 834, 860 may be pushed or otherwise moved through lumen 824 and out of the opening 828 of the distal end 830 of the introducer tube 822. In the extended position (FIGS. 11A and 11B), the second and third electrodes 834, 860 extend at least partially beyond the distal end 830 of the first electrode 826. The second and third electrodes 834, 860 may have piercing ends 850.

When the second and third electrodes 834, 860 are extended from the introducer tube 822 and into the extended positions, the second and third electrodes 834, 860 may curve or form a spiral, coil, or helix. As described above with respect to FIGS. 1A-1C, the second and third electrodes 834, 860 may comprise a superelastic material (e.g., Nitinol), though other materials may also be used. In the illustrated example, the second and third electrodes 834, 860 each form a coil once deployed within the patient's anatomy. The second and third electrodes 834, 860 may have, for example, a flat, ribbon shape or an ovular shape. Each of the second and third electrodes 834, 860 define one or more helical turns 835. In this example, each electrode 834, 860 has one helical turn 835, however, a greater number of helical turns 835 could be used alternatively. In the arrangement shown in FIGS. 11A and 11B, each electrode 834, 860 extends a shorter distance into tissue as compared to some of the other previously described electrodes. The combination of the two electrodes provides sufficient surface area to transmit a desired current to the tissue. And since each of the electrodes 834, 860 turns into the tissue with fewer turns than some of the other above described electrodes, each of the electrodes 834, 860 does not have to be as stiff as the previously described electrodes.

The introducer tube 822 is configured to substantially hold the second and third electrodes 834, 860 within the lumen 824 in predetermined orientations in the extended positions. In this example, the second electrode 834 extends upwardly from the first electrode 826 in the orientation of FIGS. 11A and 11B, and the third electrode 860 extends downwardly from the first electrode 826 in the orientation of FIGS. 11A and 11B; thus, each electrode 834, 860 reaches a different part of tissue. Proximal parts 836 of the second and third electrode 834, 860 remain within the lumen 824 in the extended positions, and the introducer tube 822 may be keyed to hold the proximal parts 836 in a predetermined angular orientation to prevent the second and third electrodes 834, 860 from substantially rotating within the lumen 824 of the introducer tube 822 during movement into the extended positions and when the second and third electrodes 834, 860 are in the extended positions as shown in FIGS. 11A and 11B.

For example, in the medical device system 800 of FIGS. 11A and 11B, the introducer tube 822 may have a neck portion with an ovular hollow cross-section. Each of the second and third electrodes 834, 860 may have corresponding cross-sections that fit together through the neck portion, such as ovular or flat cross-sections. As such, the second and third electrodes 834, 860 are keyed to the introducer tube 822 at least at the distal end 830 of the introducer tube 822. This is because the inner perimeter of the neck portion of the introducer tube 822 corresponds to part of the outer perimeters of the second and third electrodes 834, 860. Thus, the portions of the second and third electrodes 834, 860 that are disposed in the lumen 824 are prevented from substantially rotating with respect to the introducer tube 822. In other words, if the second and third electrodes 834, 860 began to rotate within the lumen 824, the second and third electrodes 834, 860 would contact an inner wall in the neck portion 852 of the introducer tube 822 which may be provided with a keying feature and which may prevent the second and third electrodes 834, 860 from further rotation.

The first, second, and third electrodes 826, 834, 860 may be used for multipolar electrode treatment. For example, electricity may pass between the second and third electrodes 834, 860, the second and third electrodes 834, 860 and the first electrode 826, or any combination thereof. It is contemplated that more than two electrodes may pass through an outer electrode and pass through a keyhole and be correspondingly keyed such that they exit the distal most end at a desired angle or set of angles.

Turning now to FIGS. 12 and 13A-13D, another example of a coil 900 employed with a medical device system 920 is illustrated. It should be understood that the medical device system 920 may be used similarly to the medical device systems 120, 20, 320, 420 and 800, as well as the introducer tubes 222 and 522, described above, if desired. In addition, the medical device system 920 may serve as an electrode assembly, as described above. All other details not described with respect to FIGS. 11A and 11B may be similar or the same as the features described with respect to the examples in FIGS. 1A-6 and 11A and 11B.

The medical device system 920 has an introducer tube 922, which defines a lumen 924 therein. The introducer tube 922 bears a first electrode 926. As such, the introducer tube 922 may itself be the first electrode 926, as shown in FIGS. 13A-13D, or the first electrode 926 may be attached to the introducer tube 922. The first electrode 926 defines an opening 928 at a distal end 930 of the first electrode 926. The first electrode 926 may be in the form of a hollow needle having a piercing tip 932.

The coil 900 forms a second electrode 934 that is movably disposed in the lumen 924 of the first electrode 926. FIGS. 13A-13D illustrate extended positions of the second electrode 934, though it should be understood that the second electrode 934 may be retracted into retracted positions similar to that shown in FIG. 1A. In the retracted positions, the second electrode 934 is disposed, or substantially disposed, within the lumen 924 of the introducer tube 922. The portion of the second electrode 934 disposed in the lumen 924 includes an extended axial portion 938 with one or more twists 940. The second electrode 934 is movable within the first electrode 926 and the introducer tube 922 between the retracted positions (similar to FIG. 1A) and the extended positions (illustrated in FIGS. 13A-13D). When it is desired to extend the second electrode 934 from the first electrode 926, the second electrode 934 may be pushed or otherwise moved through lumen 924 and out of the opening 928 of the distal end 930 of the introducer tube 922. In the extended positions (FIGS. 13A-13D), the second electrode 934 extends at least partially beyond the distal end 930 of the first electrode 926. The second electrode 934 may have a piercing end 950.

Figure 13A:
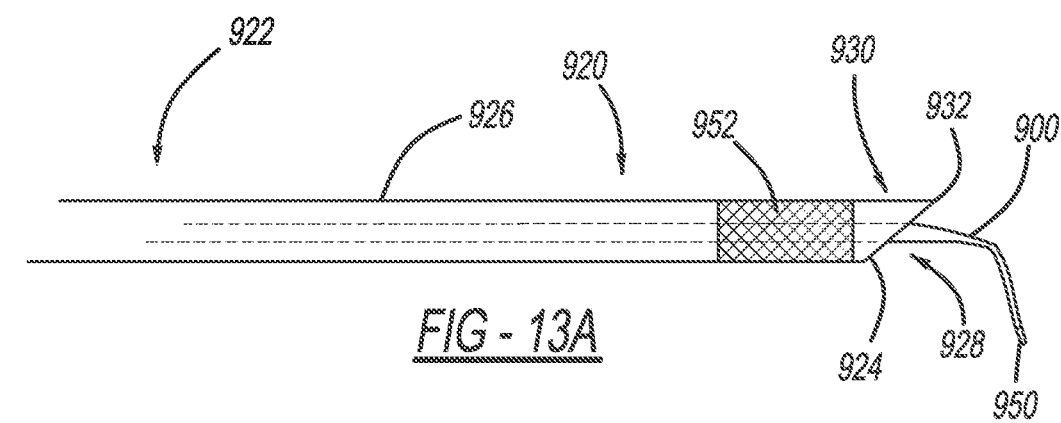
FIGS. 13A-13D are schematic side views of the electrode of FIG. 12 shown with a medical device system during deployment of the electrode, in accordance with the principles of the present disclosure.
Figure 13B:
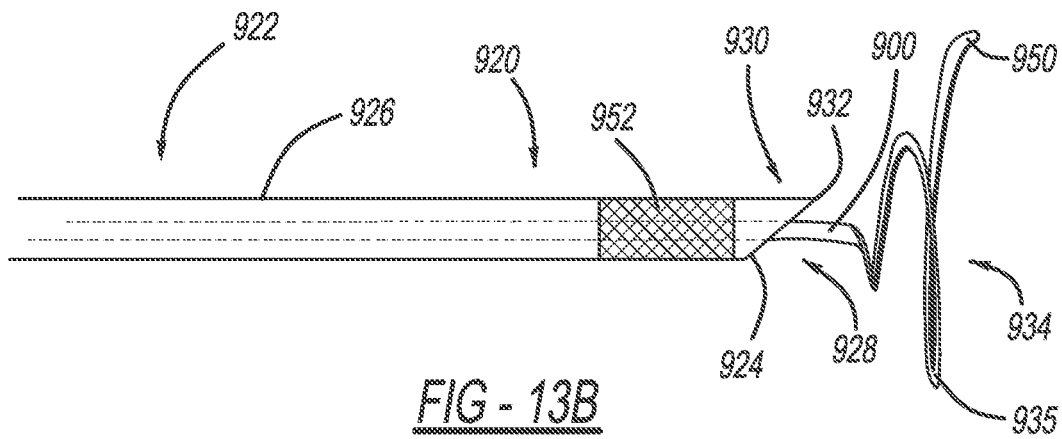
Figure 13C:
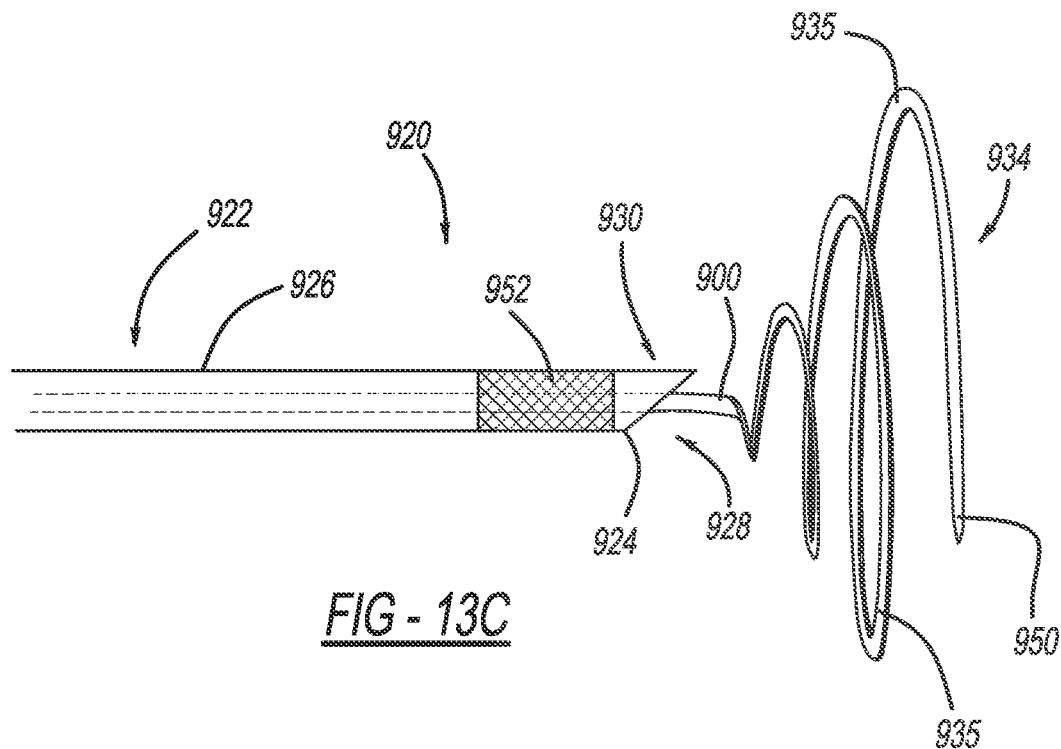
Figure 13D:
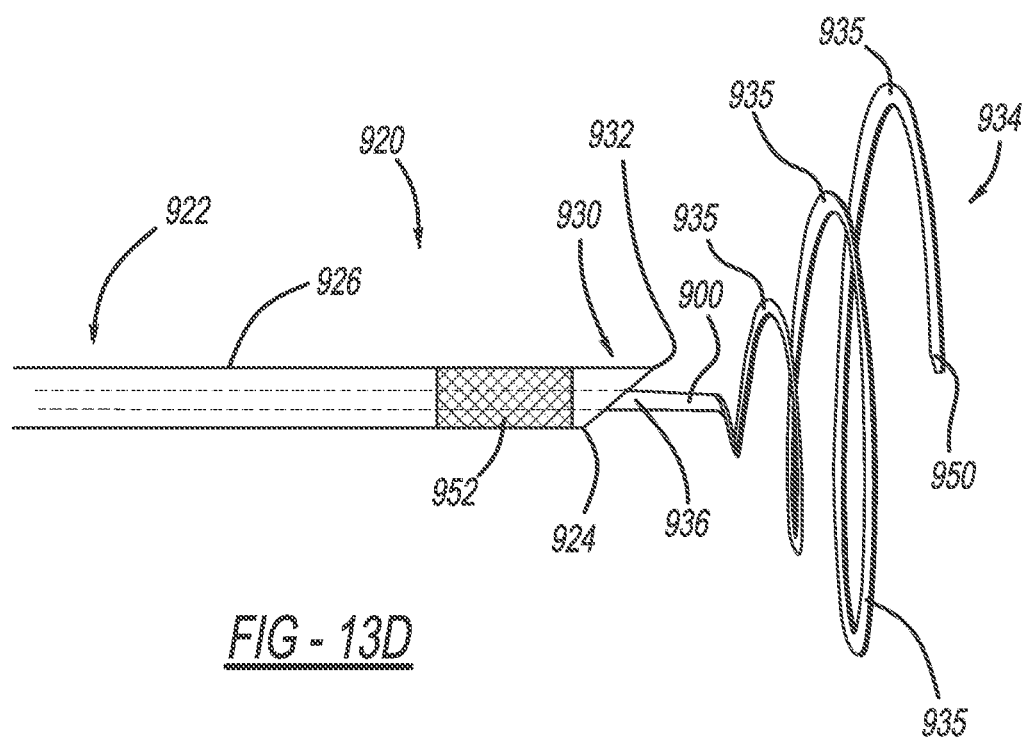

When the second electrode 934 is extended from the introducer tube 922 and into the extended positions, the second electrode 934 may curve or form a spiral, coil, or helix. As described above with respect to FIGS. 1A-1C, the second electrode 934 may comprise a superelastic material (e.g., Nitinol), though other materials may also be used. In the illustrated example, the second electrode 934 forms a coil once deployed within the patient's anatomy. The second electrode 934 may have, for example, a flat, ribbon shape or an ovular shape. The second electrode 934 defines one or more helical turns 935. In this example, the second electrode 934 has three helical turns 935 when extended as shown in FIG. 13D, however, a greater number or smaller number of helical turns 935 could be used alternatively.

The introducer tube 922 is configured to substantially hold the second electrode 934 within the lumen 924 in predetermined orientations in the extended positions. A proximal part 936 of the second electrode 934 remains within the lumen 924 in the extended most position (FIG. 13D), and the introducer tube 922 holds the proximal part 936 in a predetermined angular orientation to prevent the second electrode 934 from substantially rotating within the lumen 924 of the introducer tube 922 during movement into the extended positions and when the second electrode is in the extended positions as shown in FIGS. 13A-13D.

In the configuration shown in FIGS. 13A-13D, the introducer tube 922 has a keyway 952 positioned within the lumen 924 near the distal end 930 of the introducer tube 922. As the second electrode 934 is pushed distally through the lumen 924, the coil 900 passes through a keyhole in the keyway 952. Accordingly, as the twists 940 of the extended axial portion 938 pass through the keyhole, the twists 940 form into helical turns 935 such that the second electrode 934 deploys axially about its longitudinal axis as the second electrode 934 turns into tissue.

The description of the invention is merely exemplary in nature and variations that do not depart from the gist of the invention are intended to be within the scope of the invention. Such variations are not to be regarded as a departure from the spirit and scope of the invention. For example, variations in the various figures can be combined with each without departing from the spirit and scope of the present disclosure.

For example, it should be understood that the embodiments disclosed herein are merely examples, and variations may occur without departing from the spirit and scope of the invention, as defined by the claims. The specific illustrations are examples and are not meant to limit the invention in any way.

The preferred embodiment of the present invention has been disclosed. A person of ordinary skill in the art would realize, however, that certain modifications would come within the teachings of this invention. Therefore, the following claims should be studied to determine the true scope and content of the invention.

Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints, the use of "about" or "approximately" in connection with a range apply to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of" to describe a combination shall include the elements, ingredients, components or steps identified, and such other elements ingredients, components or steps that do not materially affect the basic and novel characteristics of the combination.

The use of the terms "comprising" or "including" describing combinations of elements, ingredients, components or steps herein also contemplates embodiments that consist essentially of the elements, ingredients, components or steps.

What is claimed is:

1. A method of delivering energy to a patient's anatomy, the method comprising:

piercing a hollow needle into a tissue in the patient's anatomy, an outer portion of the hollow needle being a first electrode including a circular cross-sectional shape, the hollow needle including an inner sheath defining a needle lumen including a non-circular cross-sectional shape and having an opening at a distal end;

extending a second electrode from the distal end of the needle lumen within the hollow needle a first time;

activating the first electrode and the second electrode to deliver a first energy to the tissue through the first electrode and the second electrode;

retracting the second electrode into the needle lumen;

rotating the hollow needle by a predetermined number of degrees about a central axis of the distal end of the hollow needle, thus causing the second electrode within the needle lumen to also rotate by the predetermined number of degrees about the central axis;

extending the second electrode from the distal end of the hollow needle a second time; and activating the first and second electrodes to deliver a second energy to the tissue through the first and second electrodes.

2. The method of claim 1, further comprising substantially preventing the second electrode from rotating with respect to the hollow needle when the second electrode is retracted or extended from the needle lumen.

3. The method of claim 2, further comprising inserting the hollow needle through an endoscope, the rotating the hollow needle by a predetermined number of degrees about a central axis of the distal end of the hollow needle including rotating the endoscope by the predetermined number of degrees about the central axis, thus causing the hollow needle to also rotate by the predetermined number of degrees about the central axis.

4. The method of claim 3, wherein inserting the hollow needle through the endoscope includes keying an external feature of the hollow needle to an internal feature of the endoscope to prevent relative rotational movement between the endoscope and the hollow needle.

5. The method of claim 1, wherein delivering the first energy includes ablating a first region of the tissue.

6. The method of claim 5, wherein delivering the second energy includes ablating a second region of the tissue that is different from the first region of the tissue.

7. The method of claim 1, wherein the extending the second electrode includes maintaining a relative rotational position between the second electrode and the needle lumen.

8. The method of claim 7, wherein the maintaining the relative rotational position includes linearly moving a non-circular cross-section of the second electrode within the needle lumen, wherein the non-circular cross-sectional shape of the needle lumen corresponds to the non-circular cross-section of the second electrode.

9. The method of claim 1, wherein extending the second electrode includes transitioning the second electrode from a substantially straight configuration within the needle lumen to a second helix configuration in an extended position.

10. The method of claim 9, wherein extending the second electrode includes linearly advancing a substantially flat cross-sectional shape of the second electrode through the non-circular cross-sectional shape of the needle lumen that corresponds to the substantially flat cross-sectional shape of the second electrode.

11. A method of delivering energy to a tissue, the method comprising:

piercing an introducer tube into the tissue in a patient's anatomy, the introducer tube including an inner sheath and an outer sheath, the outer sheath being a first electrode and defining a circular cross-sectional shape, the inner sheath defining a lumen including a non-circular cross-section shape and an opening at a distal end of the introducer tube;

extending a second electrode from the lumen out of the distal end of the introducer tube a first time;

maintaining, during the extending, a relative rotational position between a non-circular cross-sectional shape of the second electrode and the non-circular cross-sectional shape of the lumen;

activating at least one of the first electrode and the second electrode to deliver a first energy to a first region of tissue through the first electrode and the second electrode.

12. The method of claim 11, further comprising:

retracting the second electrode into the lumen;

rotating the introducer tube by a predetermined number of degrees about a central axis of the introducer tube;

extending the second electrode from the lumen out of the distal end of the introducer tube a second time;

maintaining, during the extending, a relative rotational position between the non-circular cross-sectional shape of the second electrode and the non-circular cross-sectional shape of the lumen; and activating the first and second electrodes to deliver a second energy to a second region of the tissue through the first and second electrodes.

13. The method of claim 11, wherein the maintaining the relative rotational position includes linearly moving the non-circular cross-section of the second electrode within the lumen, wherein the non-circular cross-section of the lumen corresponds to the non-circular cross-section of the second electrode.

14. The method of claim 11, wherein extending the second electrode includes transitioning the second electrode from a substantially straight configuration within the lumen in the introducer tube to a second helix configuration in an extended position.

15. The method of claim 14, wherein extending the second electrode includes the helix configuration positioned in a first rotational direction relative to the introducer tube.

16. The method of claim 14, wherein extending the second electrode includes linearly advancing a substantially flat cross-sectional shape of the second electrode through a corresponding cross-sectional shape of the lumen in the introducer tube.

17. A method of treating a tissue, the method comprising:

delivering a hollow needle to a position adjacent the tissue, the hollow needle including a first electrode and a second electrode, the second electrode positioned within a lumen formed in an inner sheath within the hollow needle, wherein the lumen within the inner sheath includes a non-circular cross-sectional shape and the hollow needle includes a circular outer cross-sectional shape;

extending the second electrode out of the hollow needle via the lumen into a first position with a first rotational orientation relative to a longitudinal axis running through the hollow needle;

retracting the second electrode back into the lumen;

rotating the hollow needle around the longitudinal axis; and extending the second electrode out of the hollow needle via the lumen into a second position with a second rotational orientation relative to the longitudinal axis.

18. The method of claim 17, wherein the second electrode includes a complementary non-circular cross-sectional shape conforming to the non-circular cross-sectional shape of the lumen in the inner sheath; and further comprising maintaining, during the extending, a relative rotational position between the non-circular cross-sectional shape of the second electrode and the non-circular cross-sectional shape of the lumen.

19. The method of claim 18, wherein extending the second electrode includes transitioning the second electrode from a substantially straight configuration within the lumen in the hollow needle to a second helix configuration in an extended position.

20. The method of claim 17, further comprising:

activating, with the second electrode in the first position, the first electrode and the second electrode to deliver a first energy to a first region of the tissue through the first electrode and the second electrode; and activating, with the second electrode in the second position, the first electrode and the second electrode to deliver a second energy to a second region of the tissue through the first electrode and the second electrode.

* * * * *